United States Patent
Schaefer et al.

(10) Patent No.: US 9,383,366 B2
(45) Date of Patent: Jul. 5, 2016

(54) BLUE FLUORESCENT PROTEIN AND METHODS OF USE THEREOF

(71) Applicant: WiSys Technology Foundation, Inc., Madison, WI (US)

(72) Inventors: Wayne Schaefer, West Bend, WI (US); Ramaswamy Subramanian, Madison, WI (US); Daniel Ferraro, O'Fallon, MO (US); Chi Li Yu, Coralville, IA (US); David Gibson, Concord, MA (US); Swagatha Ghosh, Burdwan (IN); P. Sai Sudha, Bangalore (IN)

(73) Assignee: WiSys Technology Foundation, Inc., Madison, WI (US)

( * ) Notice: Subject to any disclaimer, the term of this patent is extended or adjusted under 35 U.S.C. 154(b) by 10 days.

(21) Appl. No.: 14/207,895

(22) Filed: Mar. 13, 2014

(65) Prior Publication Data

US 2014/0272964 A1 Sep. 18, 2014

Related U.S. Application Data

(60) Provisional application No. 61/782,108, filed on Mar. 14, 2013.

(51) Int. Cl.
  *G01N 33/52* (2006.01)
  *G01N 33/58* (2006.01)
  *C07K 14/46* (2006.01)
  *G01N 33/533* (2006.01)

(52) U.S. Cl.
  CPC ............ *G01N 33/582* (2013.01); *C07K 14/461* (2013.01); *G01N 33/533* (2013.01)

(58) Field of Classification Search
  CPC ............... C12Q 2543/00; G01N 33/05; G01N 33/54386
  See application file for complete search history.

(56) References Cited

FOREIGN PATENT DOCUMENTS

WO 2008145301 A1 12/2008

OTHER PUBLICATIONS

PCT International Search Report and Written Opinion, PCT/US2014/025398, Aug. 22, 2014.
Abraham, et al., Pharmacological and Clinical Aspects of Heme Oxygenase, Pharamacological Reviews, 2008, 60(1):79-127.
Allanson, et al., Ultraviolet A (320-400 nm) Modulation of Ultraviolet B (290-320 nm)-Induced Immune Suppression is Mediated by Carbon Monoxide, J. Invest. Dermatol., 2005, 124:644-650.
Arkin, et al., Applications of Imaging Spectroscopy in Molecular Biology II. Colony Screening Based on Absorption Spectra, Bio/Technology, 1990, 8:746-749.
Bada, A Blue-Green Pigment Isolated from Blood Plasma of the Arctic Sculpin (*Myoxocephalus scorpioides*), Experientia, 1970, 26(3):251-252.
Bellner, et al., Biliverdin Rescues the HO-2 Null Mouse Phenotype of Unresolved Chronic Inflammation Following Corneal Epithelial Injury, Invest. Ophthalmol. Vis. Sci., 2011, 52:3246-3253.

(Continued)

*Primary Examiner* — Maryam Monshipouri
(74) *Attorney, Agent, or Firm* — Quarles & Brady LLP

(57) ABSTRACT

This invention provides methods of making and using a fluorescent probe from the Sandercyanin protein as set forth in SEQ ID NO: 1 or SEQ ID NO: 2. In one embodiment, the invention provides a method of creating a fluorescent probe, comprising the steps of attaching a Sandercyanin moiety to a probe, wherein the probe is specific to a desired target.

10 Claims, 26 Drawing Sheets
(26 of 26 Drawing Sheet(s) Filed in Color)

General morphology of blue and yellow forms of walleye from McKim Lake, Ontario, Canada.

(56) References Cited

OTHER PUBLICATIONS

Blazer, et al., Effects of Ultraviolet-B Radiation on Fish: Histologic Comparison of a UVB-Sensitive and a UVB-Tolerant Species, Journal of Aquatic Animal Health, 1997, 9(2):132-143.

Campbell, Status of the Blue Walleye, *Stizostedion vitreum glaucum*, in Canada, Canadian Field Naturalist, 1987, 101(2):245-252.

Chiesa, et al., Recombinant Aequorin and Green Fluorescent Protein as Valuable Tools in the Study of Cell Signaling, Biochem. J., 2001, 355:1-12.

Chivers, et al., Epidermal 'Alarm Substance' Cells of Fishes Maintained by Non-Alarm Functions: Possible Defence Against Pathogens, Parasites and UVB Radiation, Proc. R. Soc. B, 2007, 274:2611-2619.

Cubitt, et al., Understanding, Improving and Using Green Fluorescent Proteins, Trends in Biochemical Sciences, 1995, 20(11):448-455.

Deheyn, et al., Internal and Secreted Bioluminescence of the Marine Polychaete Odontosyllis Phosphorea (Syllidae), Invertebrate Biology, 2009, 128(1):31-45.

Dunlap, et al., Ultraviolet Radiation-Absorbing Mycosporine-Like Amino Acids in Coral Reef Organisms: A Biochemical and Environmental Perspective, J. Phycol., 1998, 34:418-430.

Elassiuty, et al., Heme Oxygenase-1 Expression Protects Melanocytes from Stress-Induced Cell Death: Implications for Vitiligo, Exp. Dermatol., 2011, 20(6):496-501.

Fabacher, et al., Skin Component May Protect Fishes From Ultraviolet-B Radiation, Environmental Science and Pollution Research, 1995, 2(1):30-32.

Fang, The Novel Biliverdin-Protein Complex in the Blue-Green Serum of Wooly Sculpin, *Clinocottus analis* (Pisces: Cottidae).—A Blood Biliprotein with a Different Binding Character, Bulletin of the Institute of Zoology Academia Sinica, 1985, 24(2):155-164.

Fang, et al., A Comparative Study of he Occurrence, Extent of Conjugation, and Excretion of the Bile Pigment Biliverdin in Marine Fish, Marine Biology Letters, 1983, 4:341-348.

Flower, The Lipocalin Protein Family: Structure and Function, Biochem. J., 1996, 318:1-14.

Frankenberg, et al., Biosynthesis and Biological Functions of Bilins, In: The Porphyrin Handbook, vol. 13, Chlorophylls and Bilins: Biosynthesis, Synthesis, and Degradation, K.M. Kadish, et al., Editors, Copyright 2003 Elsevier Science (USA), pp. 211-235.

Gagnon, Serum Biliverdin as Source of Colouration Upon Sexual Maturation in Male Blue-Throated Wrasse *Notolabrus tetricus*, Journal of Fish Biology, 2006, 68(6):1879-1882.

Hansson, Plasticity in Pigmentation Induced by Conflicting Threats from Predation and UV Radiation, Ecology, 2004, 85(4):1005-1016.

Hansson, et al., Effects of Ultraviolet Radiation on Pigmentation, Photoenzymatic Repair, Behavior, and Community Ecology of Zooplankton, Photochemical & Photobiological Sciences, 2009, 8:1266-1275.

Inoue, et al., Compact Packing of Lipocalin-Type Prostaglandin D Synthase Induced by Binding of Lipophilic Ligands, Journal of Biochemistry, 2009, 145(2):169-175.

Jonsson, et al., Foraging Success of Juvenile Pike *Esox lucius* Depends on Visual Conditions and Prey Pigmentation, Journal of Fish Biology, 2011, 79:290-297.

Kerr, et al., Evidence for Large Upward Trends of Ultraviolet-B Radiation Linked to Ozone Depletion, Science, 1993, 262:1032-1034.

Kollias, et al., New Trends in Photobiology: Photoprotection by Melanin, Journal of Photochemistry and Photobiology B: Biology, 1991, 9(2):135-160.

Lagarias, et al., Self-Assembly of Synthetic Phytochrome Holoprotein In Vitro, Proc. Natl. Acad. Sci. USA, 1989, 86:5778-5780.

Lamparter, et al., Phytochrome from Agrobacterium Tumefaciens Has Unusual Spectral Properties and Reveals an N-Terminal Chromophore Attachment Site, PNAS, 2002, 99(18):11628-11633.

Laporte, et al., Genetic Differentiation Between the Blue and the Yellow Phenotypes of Walleye (*Sander vitreus*): An Example of Parallel Evolution, Ecoscience, 2011, 18(2):124-129.

Leclercq, et al., Morphological Skin Colour Changes in Teleosts, Fish and Fisheries, 2010, 11(2):159-193.

Manney, et al., Unprecedented Arctic Ozone Loss in 2011, Nature, 2011, 478:469-475.

Marrot, et al., Molecular Responses to Stress Induced in Normal Human Caucasian Melanocytes in Culture by Exposure to Simulated Solar UV, Photochemistry and Photobiology, 2005, 81(2):367-375.

Murphy, et al., The Phytofluors: A New Class of Fluorescent Protein Probes, Current Biology, 1997, 7:870-876.

Paradis, et al., Phenotypic Variation of Walleye, *Sander vitreus*, in Canadian Shield Lakes: New Insights on Percid Polymorphism, Environmental Biology of Fishes, 2005, 73(4):357-366.

Pickering, et al., Sacciform Cells in the Epidermis of the Brown Trout, *Salmo trutta*, and the Arctic Char, *Salvelinus alpinus*, Cell and Tissue Research, 1987, 247(2):259-265.

Rastogi, et al., Photoprotective Compounds from Marine Organisms, Journal of Industrial Microbiology & Biotechnology, 2010, 37(6):537-558.

Reeve, et al., Radiation Sources Providing Increased UVA/UVB Ratios Induce Photoprotection Dependent on the UVA Dose in Hairless Mice, Photochemistry and Photobiology, 2006, 82:406-411.

Reeve, et al., Heme Oxygenase Induction Mediates the Photoimmunoprotective Activity of UVA Radiation in the Mouse, Proc. Natl. Acad. Sci. USA, 1999, 96:9317-9321.

Schmitz, Dissertation: Sensitivity of the Atlas Experiment to Discover the Decay H-TT-II+4v of the Standard Model Higgs Boson Produced in Vector Boson Fusion, 2011.

Whitaker, et al., An Absolute Method for Protein Determination Based on Difference in Absorbance at 235 and 280 nm, Analytical Biochemistry, 1980, 109(1):156-159.

Whitear, II. The Skin of Fishes Including Cyclostomes, Chapter 2. Epidermis, In: Biology of the Integument, 2 Vertebrates, Edited by Bereiter-Hahn, et al., Copyright by Springer-Verlag Berlin Heidelberg, 1986, pp. 8-64.

Yamaguchi, et al., Identity of Blue Pigments Obtained from Different Tissues of the Sculpin, *Pseudoblennius percoides* Gunther, Comparative Biochemistry and Physiology, 1976, 55B(1):85-87.

Yannarelli, et al., Heme Oxygenase Up-Regulation in Ultraviolet-B Irradiated Soybean Plants Involves Reactive Oxygen Species, Planta, 2006, 224(5):1154-1162.

Yu, et al., Purification and Properties of Sandercyanin, a Blue Protein Secreted in the Mucus of Blue Forms of Walleye, *Sander vitreus*, Environ. Biol. Fish, 2008, 82:51-58.

Zagarese, et al., The Implications of Solar UV Radiation Exposure for Fish and Fisheries, Fish and Fisheries, 2001, 2(3):250-260.

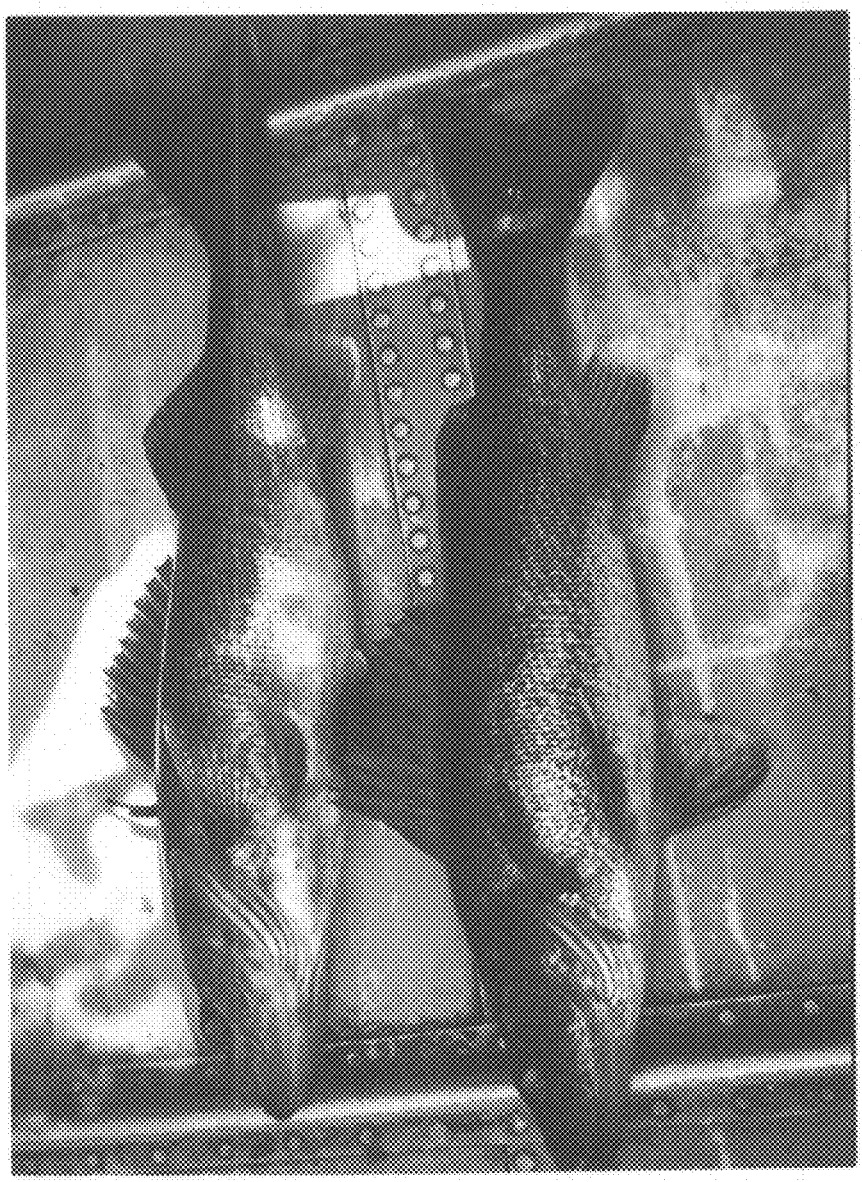
Figure 1. General morphology of blue and yellow forms of walleye from McKim Lake, Ontario, Canada.

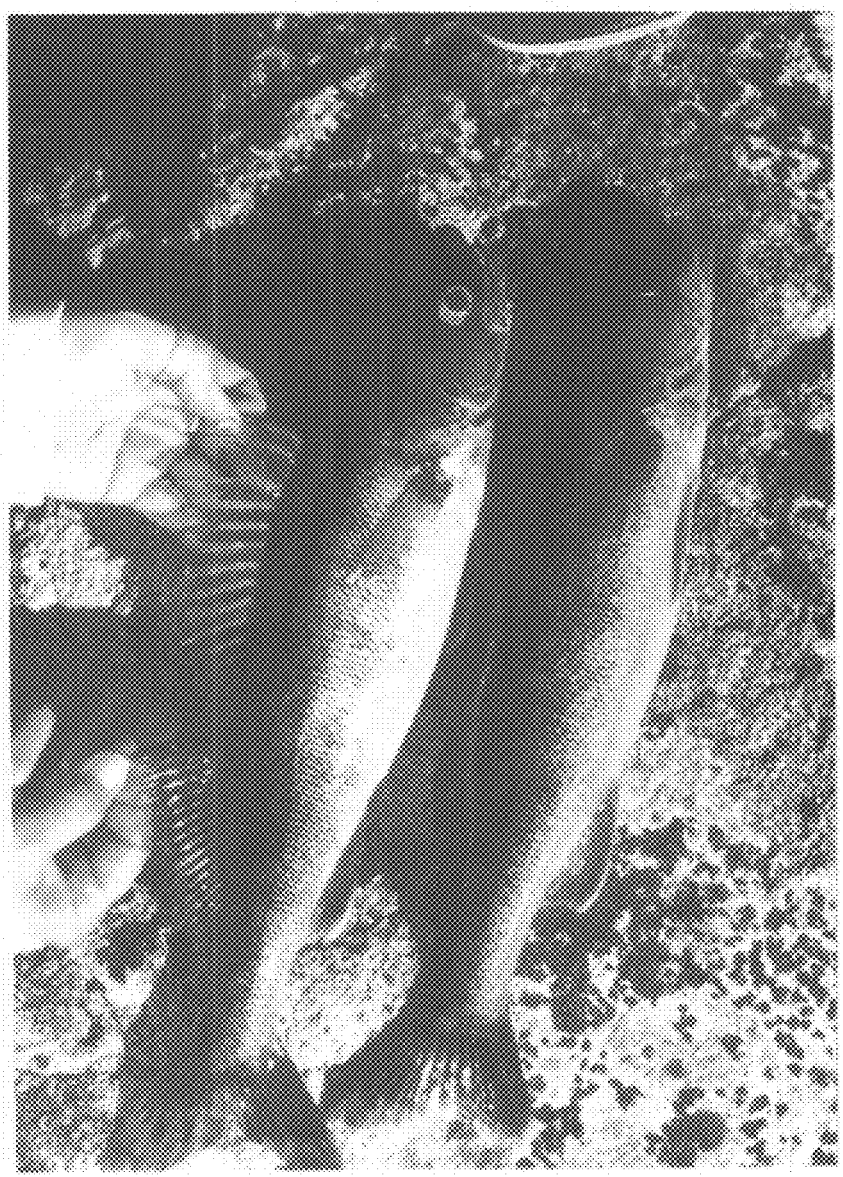
Figure 2. Translucent fins on blue walleye containing no yellow pigment.

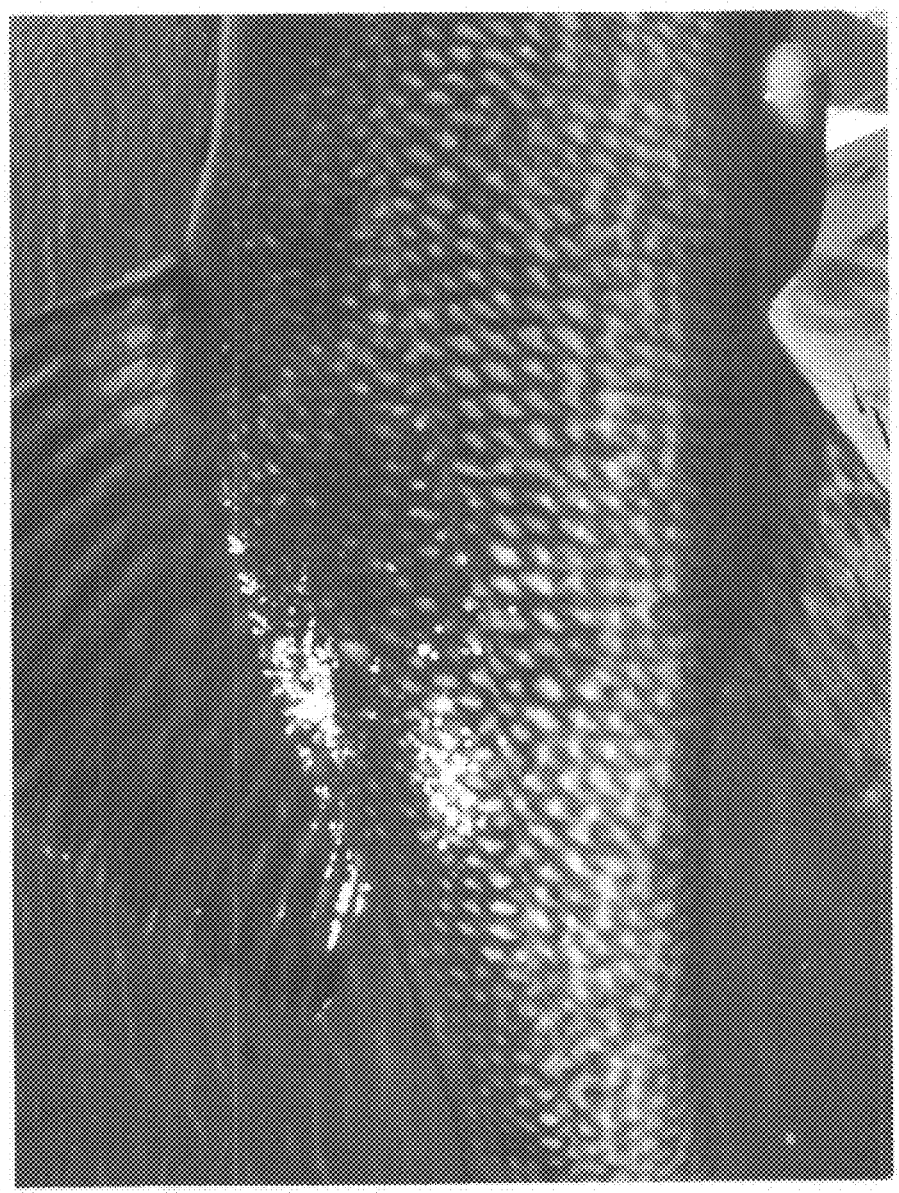
Figure 3. Blue pigment is confined to the dorsal side of the fish.

Figure 4. Blue lines of Sandercyanin posterior to each dorsal spine.

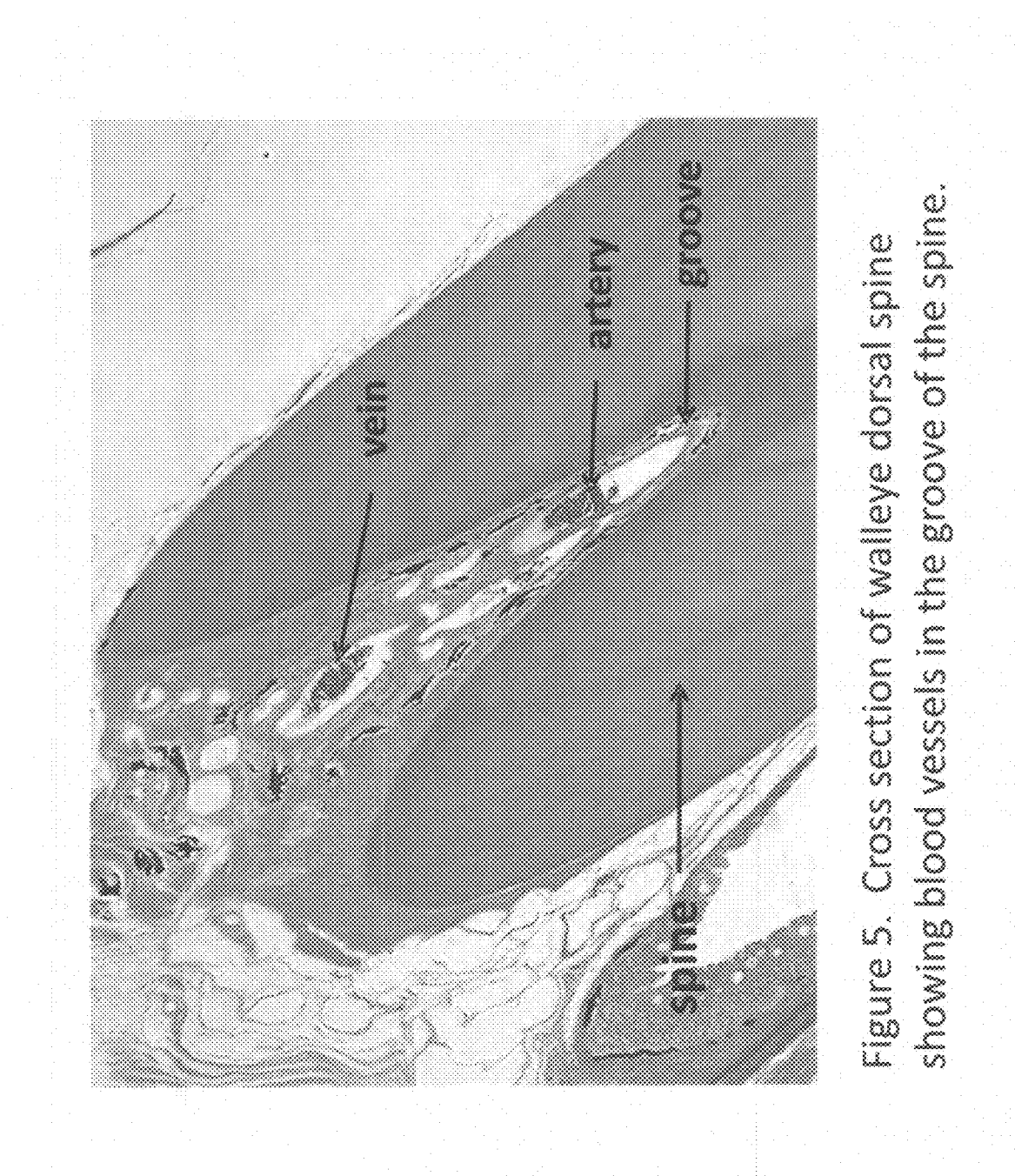
Figure 5. Cross section of walleye dorsal spine showing blood vessels in the groove of the spine.

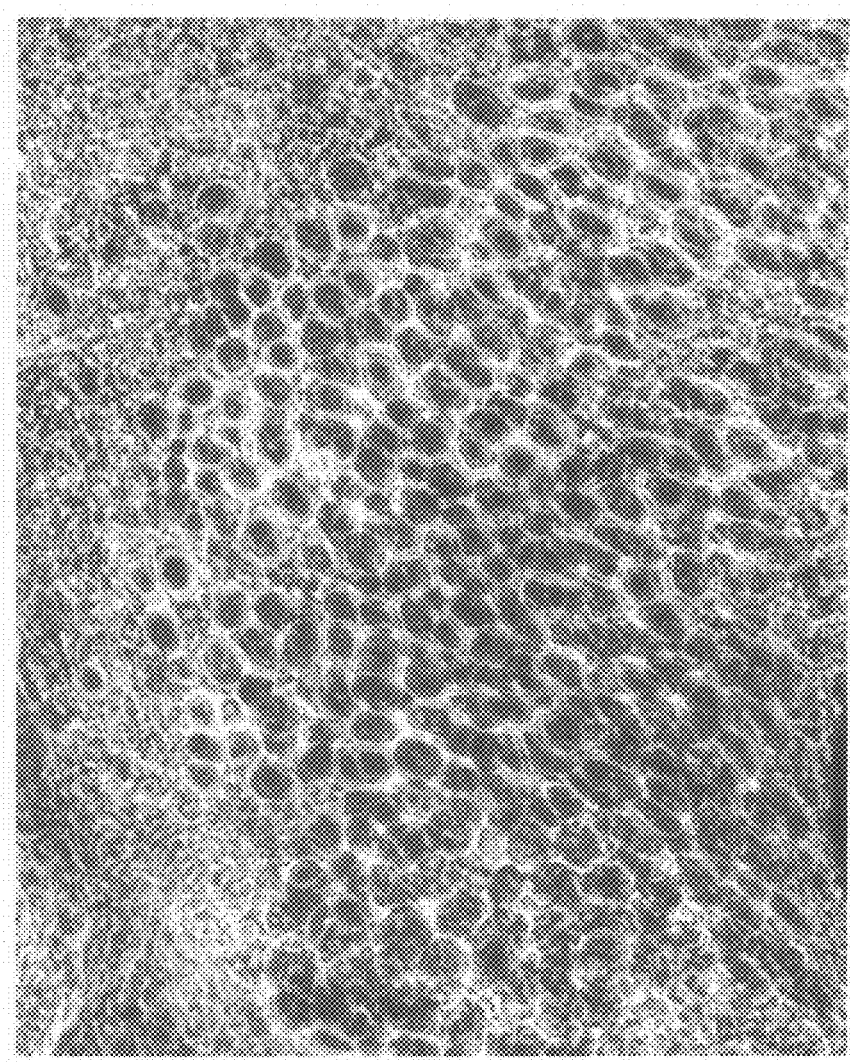
Figure 6. Sandercyanin within pigment containing cells (Sander Cells). 100X

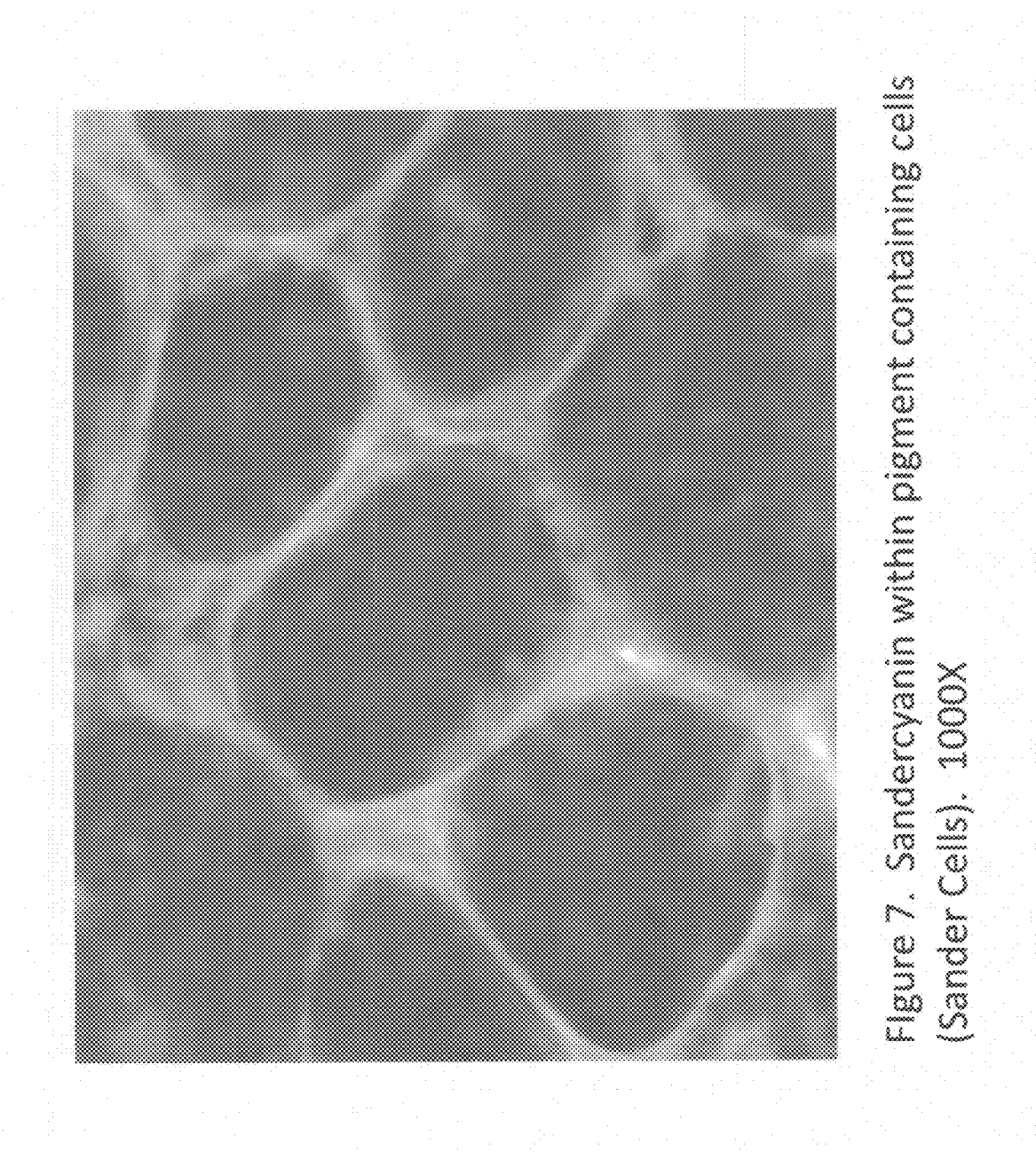
Figure 7. Sandercyanin within pigment containing cells (Sander Cells). 1000X

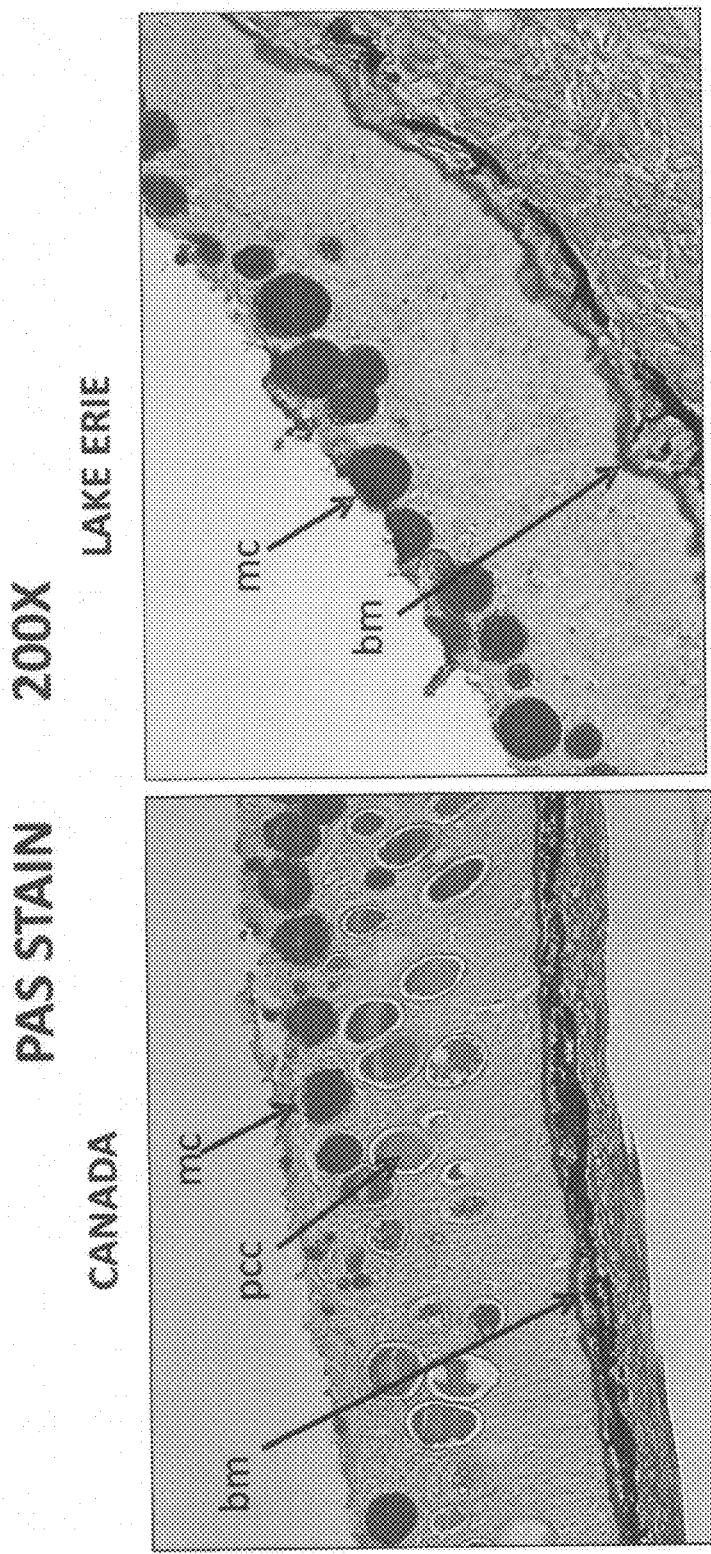
Figure 8. Epidermal cross section of Canadian walleye producing Sandercyanin (left) and control walleye from Lake Erie not producing Sandercyanin (right). Both samples were captured in August of 2010. bm = basement membrane of epithelium; pcc = pigment containing cell; mc = mucus cell.

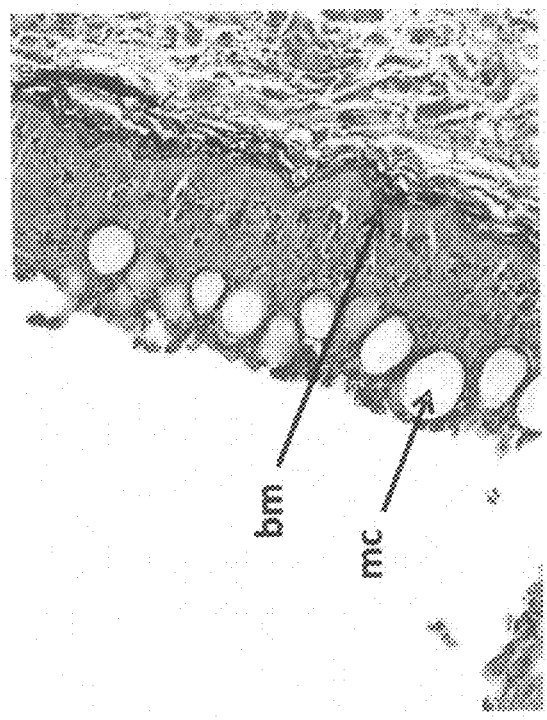
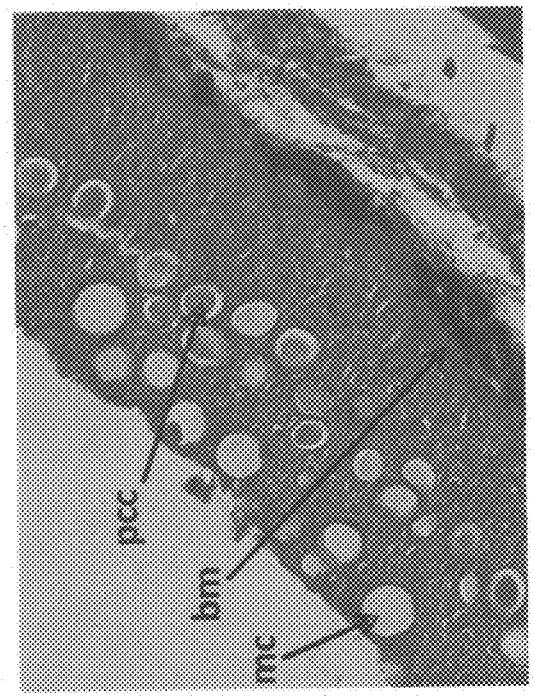
figure 9. Epidermal cross section of Canadian walleye producing Sandercyanin (left) and control walleye from Lake Erie not producing Sandercyanin (right). bm = basement membrane of epithelium; pcc = pigment containing cell; mc = mucus cell.

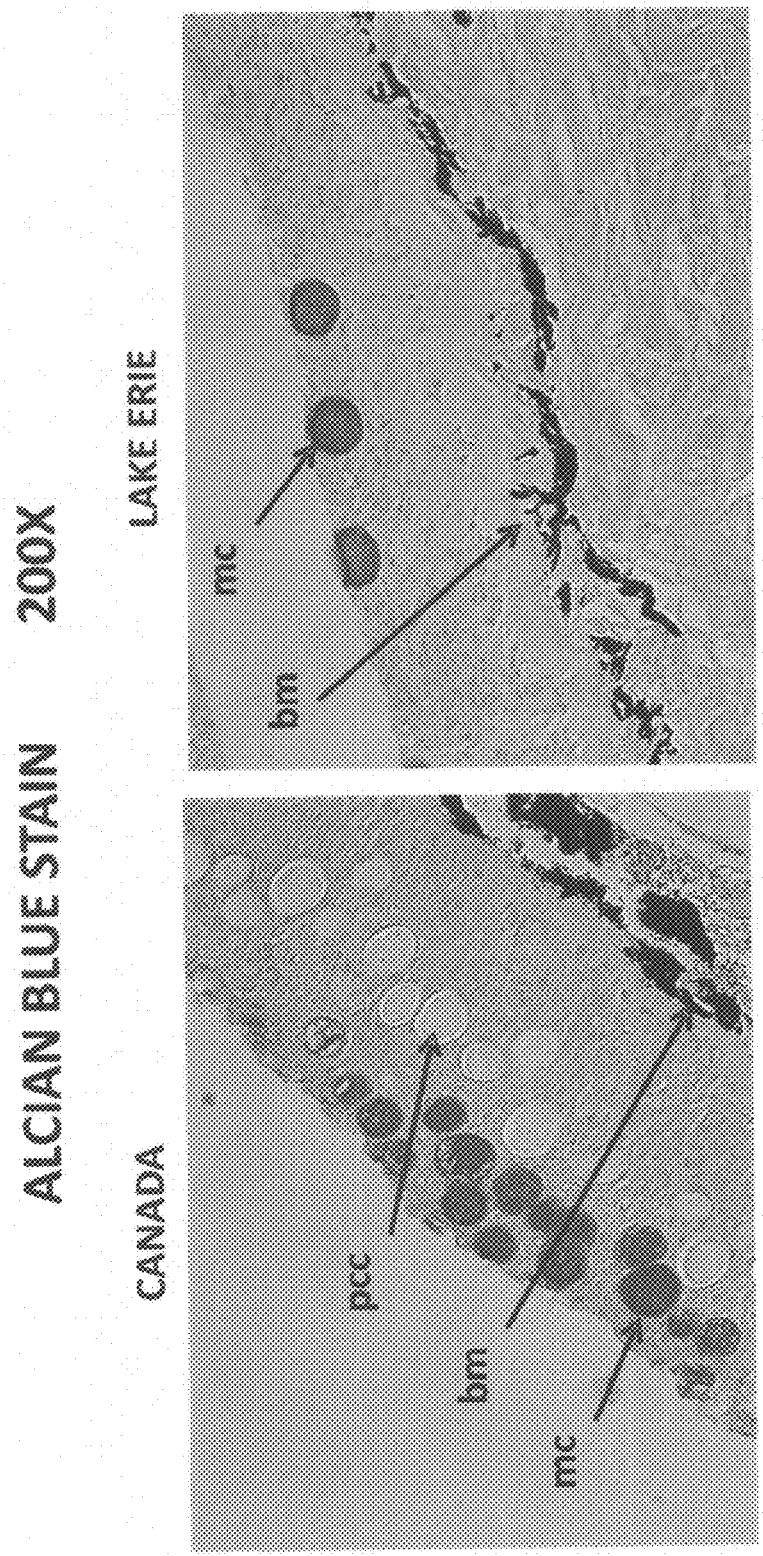
Figure 10. Epidermal cross section of Canadian walleye producing Sandercyanin (left) and control walleye from Lake Erie not producing Sandercyanin (right). bm = basement membrane of epithelium; pcc = pigment containing cell; mc = mucus cell.

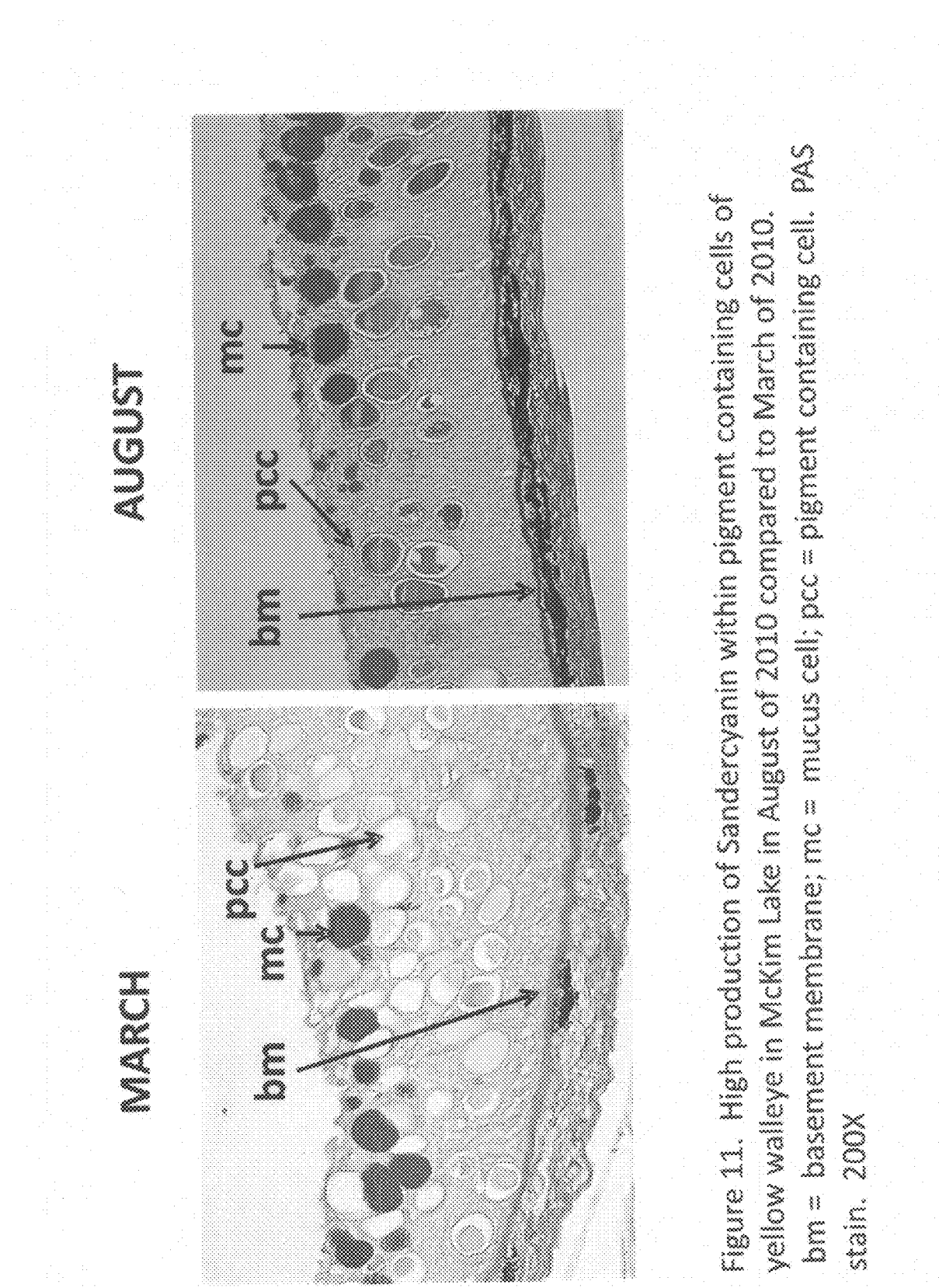
Figure 11. High production of Sandercyanin within pigment containing cells of yellow walleye in McKim Lake in August of 2010 compared to March of 2010. bm = basement membrane; mc = mucus cell; pcc = pigment containing cell. PAS stain. 200X

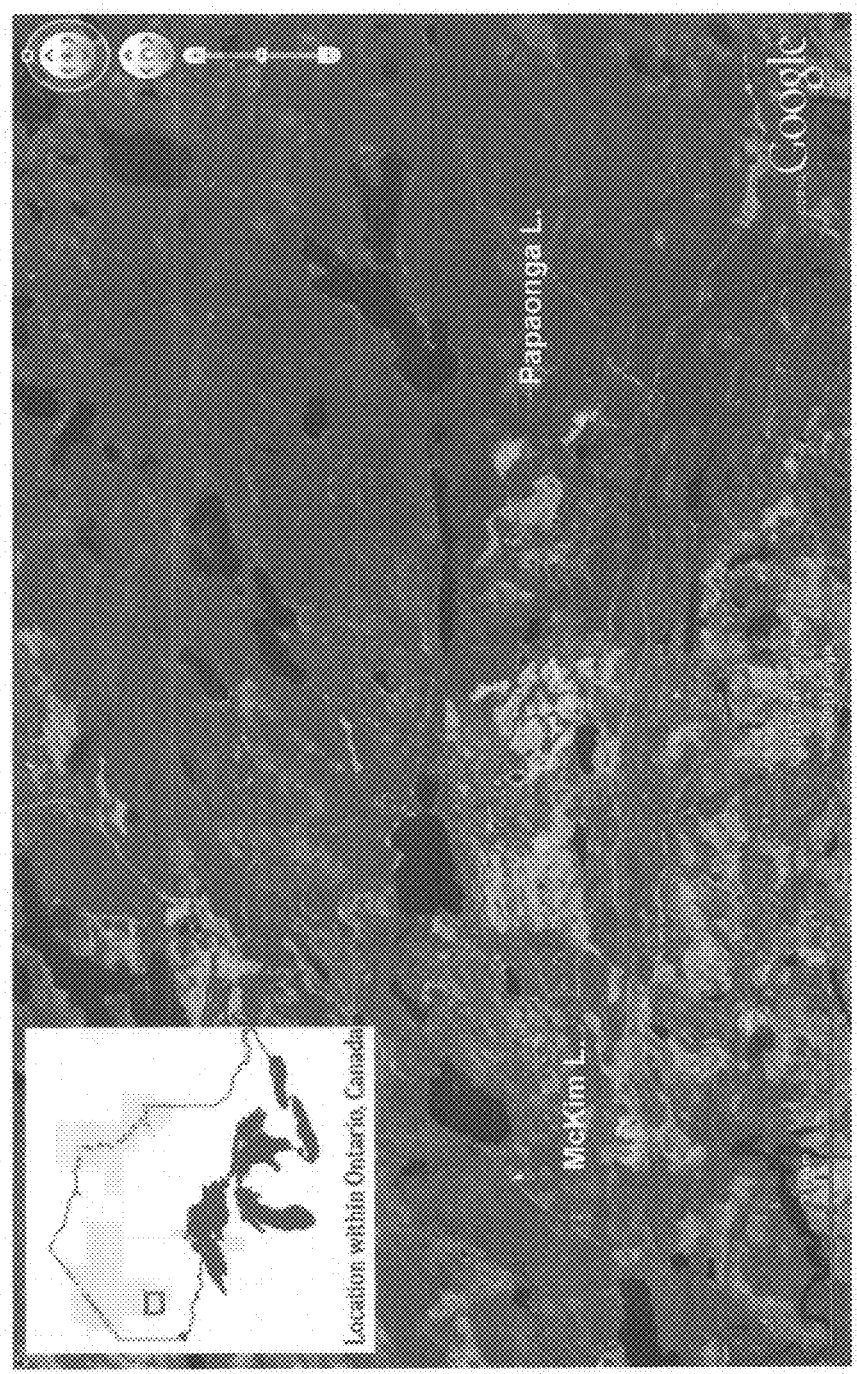
Figure 12. Location of McKim Lake relative to Papaonga Lake within the Papaonga River system in northwestern Ontario.

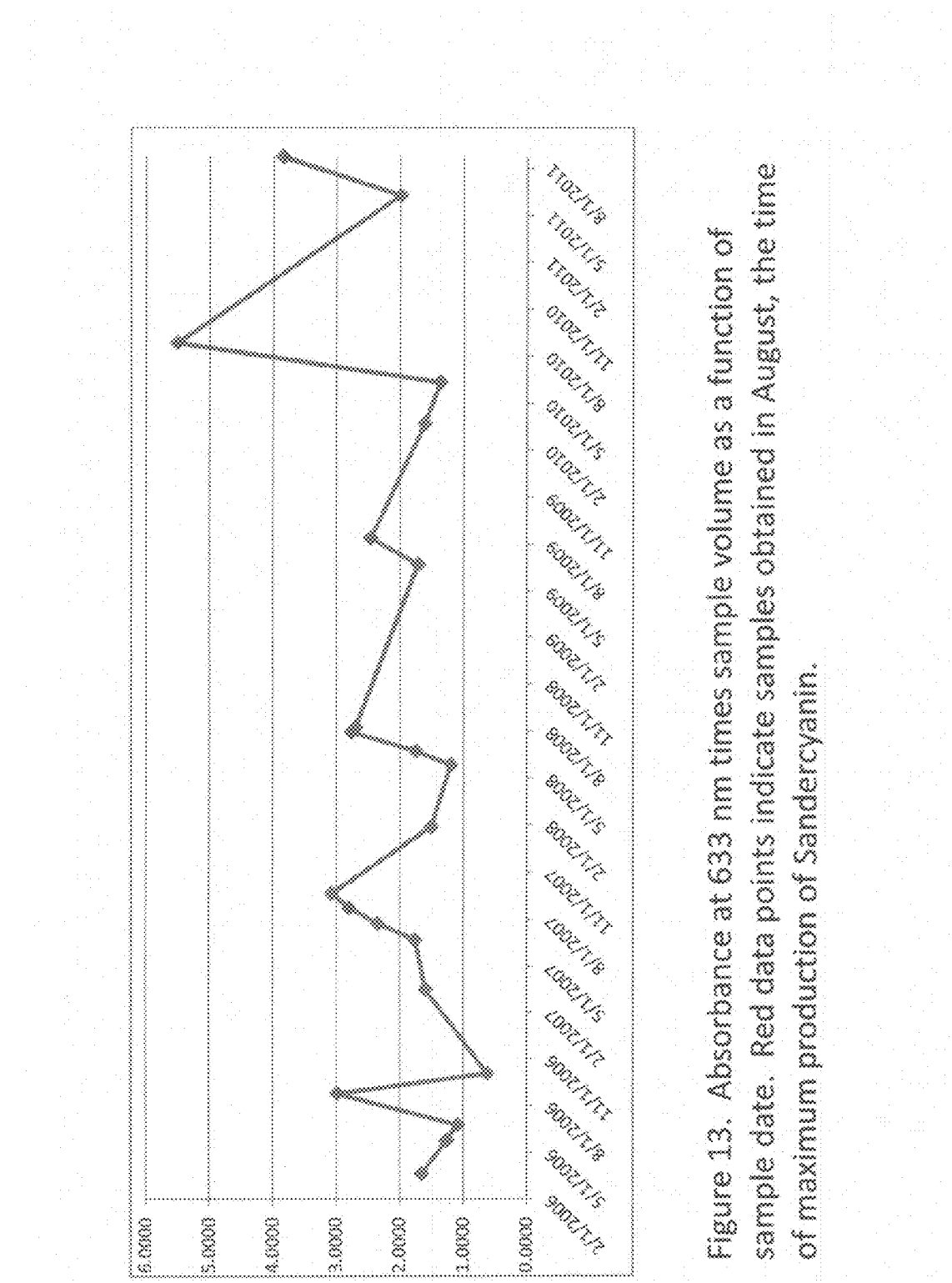
Figure 13. Absorbance at 633 nm times sample volume as a function of sample date. Red data points indicate samples obtained in August, the time of maximum production of Sandercyanin.

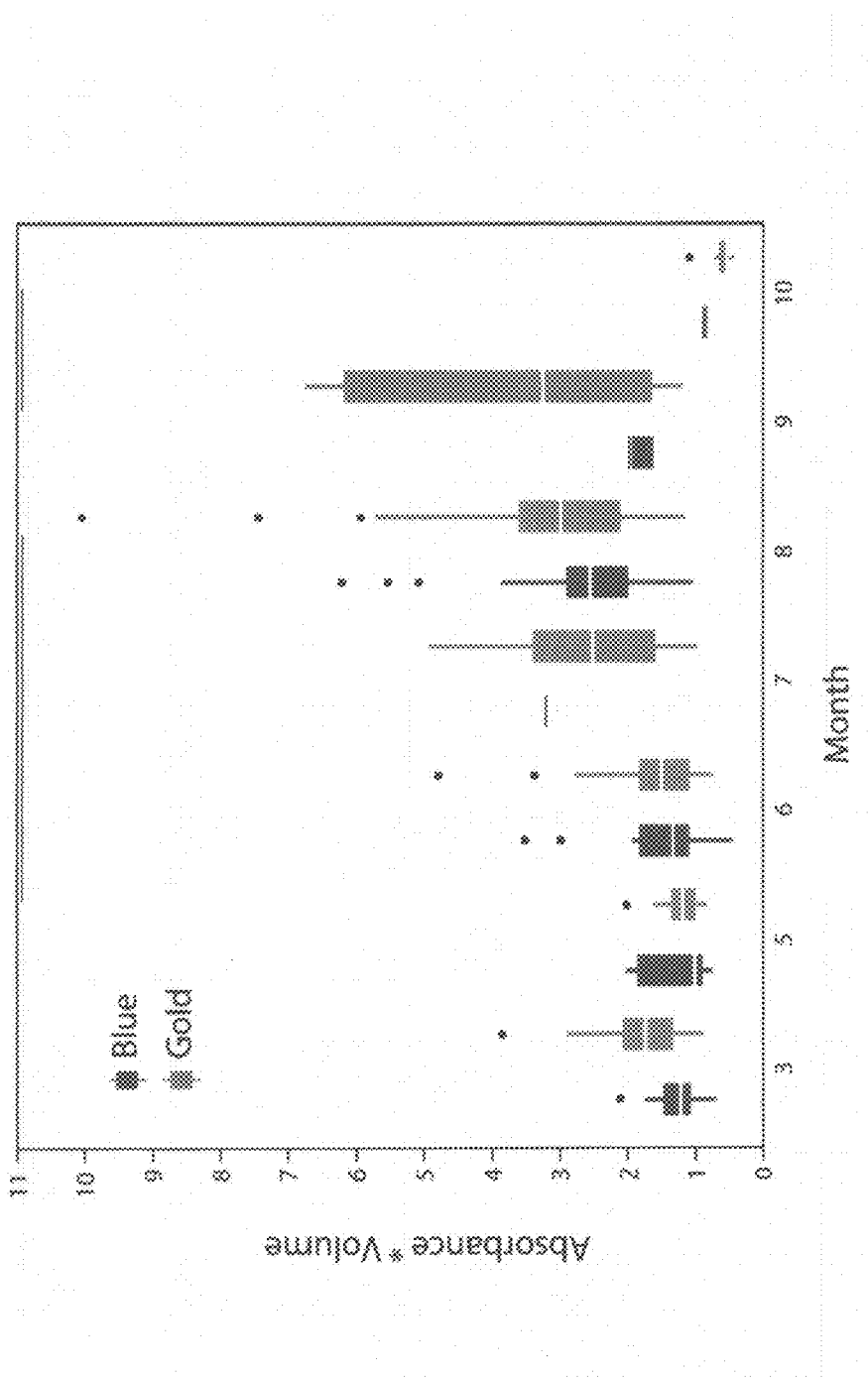
Figure 14. Box plots representing the amount of Sandercyanin present in blue and gold walleye from McKim Lake from January to October. Mean absorbance was multiplied by sample volume to determine the total amount of Sandercyanin present. Monthly data was pooled across a 6-year period.

PROTEIN SEQUENCE WITHOUT SIGNAL PEPTIDE

QFIMPGRCPKPAVQEDFDAARYLGVWYDIQRLPNKFQKGECATATY
SLSPGVGFSVFNRERLANGTIKSVIGSAIAEDPCEPAKLQFFHENAAP
VPYWVLSTDYDNYALVYSCINLGASHAAYASIVSRQPTLPEETIKKLQ
GTMSSFGVGVDTLLTTNQDAAYCSAMNQ

Biliverdin IXα binding pocket: An insight from the crystal structure
(Taken from the crystal structure)
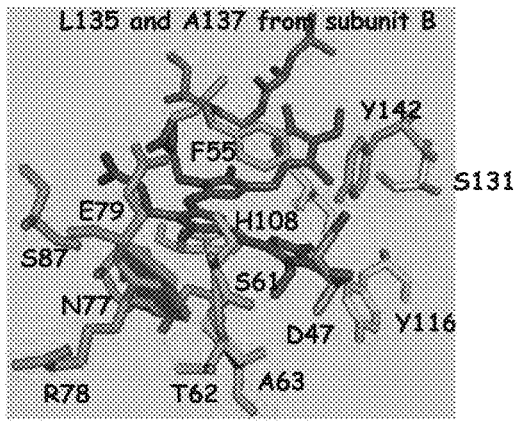
(Reference: Ramaswamy S. et al, University of IOWA, 2007)
Figure 17
Imaging experiments with Sandercyanin
Visualization of mucus cell from blue fish,
$\lambda_{ex}$= 360 nm (DAPI),
$\lambda_{em}$= 675nm (Cy5 filter)
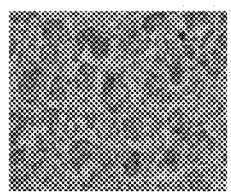
Bright field image
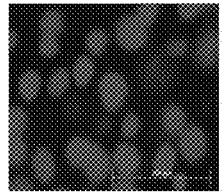
Image under Cy5 filter
Figure 18

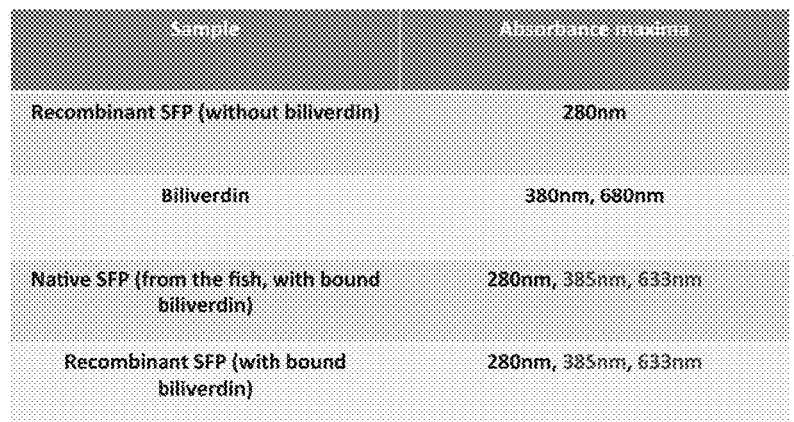
Figure 23
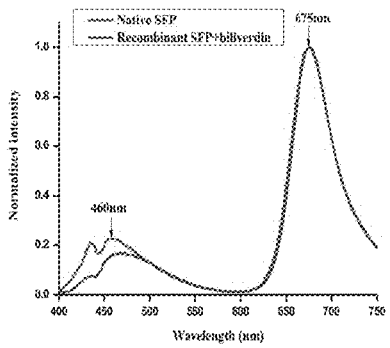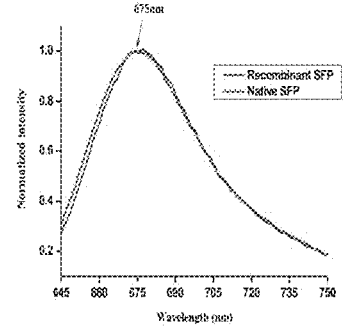
Figure 24

Fluorescence spectra of rSFP overlaps with the native protein (nSFP) from fish

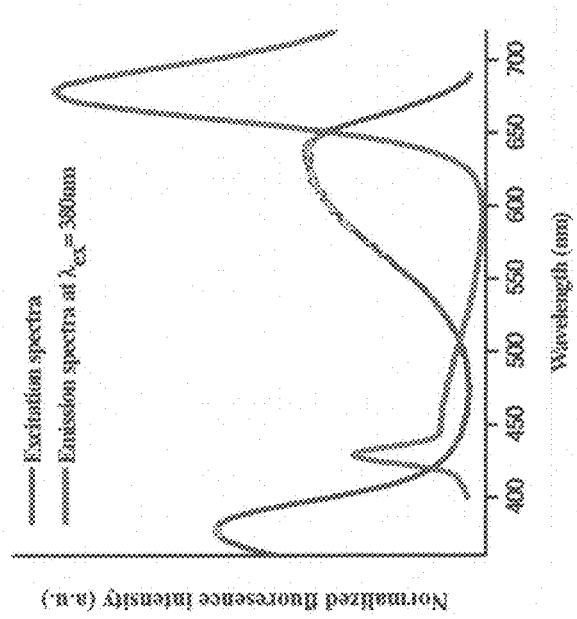
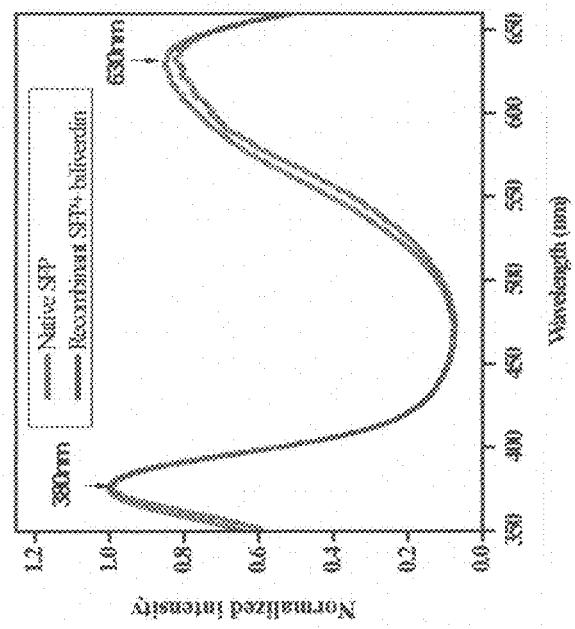
Figure 31

Native protein, when injected into hydra (a model system to study regeneration), showed fluorescence on the surface of tentacles.

$\lambda_{ex} = 405$ nm (DAPI) and $\lambda_{em} = 675$nm (Cy5 filter)

A table comparing advantages of recombinant protein over the native protein.

| Features | Recombinant protein | Native protein |
|---|---|---|
| Protein engineering and gene transfection into cell-lines | Possible | Not possible |
| Glycosylation | Absent, hence can be expressed in any system | Present |
| Protein production | Large amounts can be expressed and purified in lab for experiments | Comes from a rare fish, cannot by purified in large quantities |

Figure 33

BLUE FLUORESCENT PROTEIN AND METHODS OF USE THEREOF

CROSS-REFERENCE TO RELATED APPLICATIONS

This application claims the benefit of U.S. Provisional Application No. 61/782,108 filed Mar. 14, 2013 which is incorporated by reference herein in its entirety for all purposes.

STATEMENT REGARDING FEDERALLY SPONSORED RESEARCH OR DEVELOPMENT

Not applicable.

BACKGROUND

Production of color in fish is generally limited to the dermal and epidermal regions of the skin, where chromatophores specialize in the synthesis and storage of light absorbing pigments (Fujii 1993; reviewed in Leclercq et al. 2010). In the case of walleye, *Sander vitreus*, color in some populations is a result of both the underlying pigmentation of the chromatophores and a blue color attributed to mucus on the outside of the fish (Regier et al. 1969, Scott and Crossman 1973). More recently, blue and yellow walleye morphotypes have been described from central Quebec, Canada (Paradis 2005) and northwestern Ontario, Canada (Yu et al. 2007) that also include blue mucus.
Native Sandercyanin Protein.

The inventors have isolated and described Sandercyanin, a novel blue protein derived from the mucus of walleye in the Papaonga River system of Ontario (Yu et al. 2007). The ecological significance of Sandercyanin has not been determined; however, it is secreted by the fish into its skin mucus. The Sandercyanin protein is a bili-binding, lipocalin protein with a molecular mass of 87,850. It is a tetramer with a subunit molecular mass of 21,386 Daltons. The Sandercyanin protein has absorption maxima at 280, 383 and 633 nm and has emission maxima at 678 nm on excitation at 380 nm and 630 nm (Yu et al. 2007). Both excitation and emission peaks are broad and have minimal spectral overlap.
Recombinant Proteins.

The importance of recombinant proteins for modern medical applications and therapy is known in the art. Recombinant production methods for bacteria are well developed and many important commercial proteins are produced in bacterial prokaryotic systems.

Recombinant DNA technology is one way of studying the functions and interactions of proteins. This is done by isolating a target DNA sequence and then transferring it to a cloning vector that has the ability to self-reproduce. The DNA of the cloning vector interacts with the target DNA and produces a new blueprint of gene information called recombinant DNA. The recombinant DNA is transcribed to RNA, which in turn produces the recombinant protein.
Color-Producing Compounds.

Bilin pigments, when associated with proteins, exhibit a wide variety of photophysical properties, i.e., intense fluorescence, photochemical interconversions, and radiation-less de-excitation. Differences in the protonation state, conformation and/or ionic environment of bilin pigments can significantly alter their absorption and emission properties. In this way, the protein moiety of bili-proteins tunes the spectrum of their bilin chromophore.

Plants, some bacteria, and fungi contain phytochromes, which are self-assembling bili-proteins that act as light sensors to modulate growth and development. Phytochromes' covalently bound bilin prosthetic groups photo-isomerize upon absorption of light, enabling the protein to photo-interconvert between two distinct species, which have absorption maxima in the red and NIR region. Unlike the intensely fluorescent phycobili-proteins, components of the photosynthetic antennae of algae, native phytochromes are non-fluorescent bili-proteins because this photo-conversion process is so efficient.

The optical properties of phytochromes are highly malleable, as shown by the spectral diversity of phytochromes in nature. In plants, algae and cyanobacteria, phytochromes are associated with the linear tetrapyrroles phytochromobilin (P.phi.B) or phycocyanobilin (PCB). Binding of an apo-phytochrome to the unnatural bilin precursor, phycoerythrobilin (PEB) however, affords a strongly fluorescent phytochrome known as a phytofluor, that is unable to isomerize upon light absorption (Murphy 1997). Phytofluors have been shown to be useful probes in living cells; however, addition of exogenous unnatural bilin precursors is generally necessary. Recently, a new class of phytochromes from bacteria and fungi was identified that attach a different bilin chromophore, biliverdin (BV), to an apparently distinct region of the apo-protein (Lamparter et al. 2002). These studies indicate that molecular evolution has occurred in nature to produce phytochrome mutants with novel spectroscopic properties.
Fluorescent Proteins.

Fluorescent proteins can be found in most molecular biology laboratories and have revolutionized the study of biology. Fluorescent probes are attractive due to their high sensitivity, good selectivity, fast response and their visual detectability. For example, the jellyfish green fluorescent protein (GFP) has revolutionized cell biological studies, allowing for the visualization of protein dynamics in real-time within living cells by in-frame fusion to a gene of interest. Other fluorescent proteins known to the art include *Aequorea coerulescens* GFP (AcGFP1), a monomeric Green Fluorescent Protein with spectral properties similar to those of EGFP (Enhanced Green Fluorescent Protein); tdTomato, an exceptionally bright and versatile red fluorescent protein that is 2.5 times brighter than EGFP; mStrawberry, a bright, monomeric red fluorescent protein which was developed by directed mutagenesis of mRFP; mRaspberry, developed by directed mutagenesis of mRFP1, a monomeric mutant of DsRed; E2-Crimson, a bright far-red fluorescent protein that was designed for in vivo applications involving sensitive cells such as primary cells and stem cells; DsRed-Monomer, an ideal fusion tag which has been expressed as a fusion with a large panel of diverse proteins with diverse functions and subcellular locations; and more.

Applications of fluorescent proteins include investigation of protein-protein interactions, spatial and temporal gene expression, assessing cell bio-distribution and mobility, studying protein activity and protein interactions in vivo, as well as cancer research, immunology and stem cell research and sub-cellular localization. Fluorescent proteins have also been used to label organelles, to image pH and calcium fluxes, and to test targeting peptides (Chiesa et al. 2001).

Despite their utility, as with any technology, existing fluorescent proteins have inherent limitations. For instance, GFP produces cytotoxic hydrogen peroxide (Cubitt et al. (1995)). Further, some fluorescent proteins are typically homo-dimers, a property that can interfere with the native function of the fused protein of interest. GFPs are also temperature and pH-sensitive and can be highly susceptible to photobleaching and oxidation. Further, GFPs are unable to fold and fluoresce in periplasmic/extra-cellular space (Jennifer et al. (2010)), hence finding limitation to be used for studying cell dynamics in the extracellular matrices.

Accordingly, a need exists for new methods of using fluorescent proteins.

SUMMARY OF THE INVENTION

This invention provides methods of making and using a fluorescent probe from the Sandercyanin protein as set forth is SEQ ID NO: 1 or SEQ ID NO: 2.

One embodiment of the invention provides a fluorescent probe and a method of preparing a fluorescent probe. The probe comprises a Sandercyanin protein moiety or a fragment thereof attached to a probe for detecting a specific target wherein, when excited, the probe emits a fluorescent signal.

In one embodiment, the protein moiety is a recombinant Sandercyanin protein or a fragment thereof, the fragment retaining the fluorescent properties of the Sandercyanin protein.

In other embodiments, the invention provides a method of using a fluorescent probe, comprising the steps of obtaining the fluorescent probe as described above, exposing the probe to a desired target, and exposing the probe and target to light having a wavelength ranging from about 350-690 nm, wherein the fluorescent probe fluoresces.

In other embodiments, the invention provides a labeled marker for detection of a target, the marker comprising a label selected from the group consisting of Sandercyanin fluorescent protein and a fluorescent variant thereof, and a ligand configured to bind to the target. The ligand may be any ligand known to the art, including, for example and without limitation, a nucleic acid probe, an antibody, biotin, avidin and streptavidin.

In still other embodiments, the invention provides a method for detecting a target comprising: providing a labeled ligand which incorporates a label selected from the group consisting of Sandercyanin fluorescent protein and a fluorescent variant thereof, and a ligand for binding the target; contacting the target with the labeled ligand; allowing the labeled ligand to bind to the target; subjecting the labeled ligand and target to light having a wavelength which excites the label; and observing the locus of fluorescence.

In other embodiments, the invention provides a method for producing an isolated recombinant protein comprising introducing DNA encoding a Sandercyanin protein or a fragment thereof into the organism, culturing the organism in an enclosed system, harvesting the organism, and isolating the recombinant protein from the organism, wherein the recombinant protein is Sandercyanin fluorescent protein. The DNA may additionally contain a promoter that is functional in the organism.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DESCRIPTION OF THE FIGURES

This patent application file contains at least one drawing executed in color. Copies of this patent or patent application publication with color drawings will be provided by the Office upon request and payment of the necessary fee.

FIG. 1 shows the general morphology of blue and yellow forms of walleye from McKim Lake, Ontario, Canada.

FIG. 2 shows the translucent fins on blue walleye containing no yellow pigment.

FIG. 3 shows that blue pigment is confined to the dorsal side of the fish.

FIG. 4 shows the Blue lines of Sandercyanin posterior to each dorsal spine.

FIG. 5 shows a cross section of walleye dorsal spine showing blood vessels in the groove of the spine.

FIG. 6 shows Sandercyanin within pigment containing cells (Sander Cells) at 100×.

FIG. 7 shows Sandercyanin within pigment containing cells (Sander Cells) at 1000×.

FIG. 8 shows an epidermal cross section of Canadian walleye producing Sandercyanin (left) and control walleye from Lake Erie not producing Sandercyanin (right). Both samples were captured in August of 2010. bm=basement membrane of epithelium; pcc=pigment containing cell; mc=mucus cell.

FIG. 9 shows an epidermal cross section of Canadian walleye producing Sandercyanin (left) and control walleye from Lake Erie not producing Sandercyanin (right). bm=basement membrane of epithelium; pcc=pigment containing cell; mc=mucus cell.

FIG. 10 shows an epidermal cross section of Canadian walleye producing Sandercyanin (left) and control walleye from Lake Erie not producing Sandercyanin (right) bm=basement membrane of epithelium; pcc=pigment containing cell; mc=mucus cell.

FIG. 11 shows High Figure production of Sandercyanin within pigment containing cells of yellow walleye in McKim Lake in August of 2010 compared to March of 2010. bm=basement membrane; mc=mucus cell; pcc=pigment containing cell. PAS stain at 200×.

FIG. 12 shows the location of McKim Lake relative to Papaonga Lake within the Papaonga River system in northwestern Ontario.

FIG. 13 shows the absorbance at 633 nm times sample volume as a function of sample date. Red data points indicate samples obtained in August, the time of maximum production of Sandercyanin.

FIG. 14 shows a box plot representing the amount of Sandercyanin present in blue and gold walleye from McKim Lake from January to October. Mean absorbance was multiplied by sample volume to determine the total amount of Sandercyanin present. Monthly data was pooled across a 6-year period.

FIG. 17 shows the ligand binding pocket of the protein.

FIG. 18 illustrates the mucus cell from blue fish A) bright field and B) under Cy5 filter.

FIG. 23 compares the spectral shift in absorbance from free biliverdin (BV) to biliverdin bound to the Sandercyanin protein.

FIG. 24 compares the emission spectra of recombinant Sandercyanin protein and Native Sandercyanin protein.

FIG. 31 shows the excitation spectra of recombinant Sandercyanin fluorescent protein (rSFP) and native Sandercyanin fluorescent protein (nSFP).

FIG. 33 compares the advantages of recombinant protein over native Sandercyanin protein.

DESCRIPTION OF THE INVENTION

Figures 15, 16:
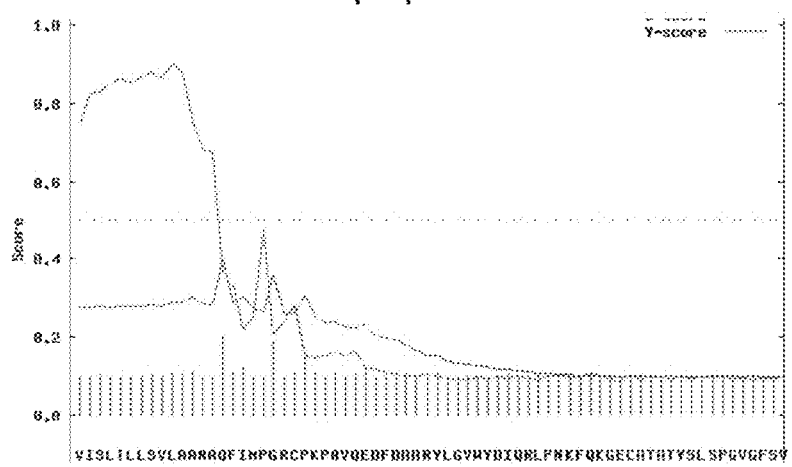
FIG. 15 shows sequence and analysis for signal peptide.
FIG. 16 shows the protein sequence without the signal peptide.

In General.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

This invention pertains to the surprising discovery that the blue fluorescent protein discovered by the inventors, Sandercyanin, as set forth in SEQ ID NO: 1, is useful for fluorescently marking a protein, cell, or organism of interest in many biochemistry, molecular biology and medical diagnostic applications. A variety of different labels exist in the art, including radiolabels, chromolabels, fluorescent labels, chemiluminescent labels, etc. There is continued interest, however, in the development of new protein labels, including chromo- and/or fluorescent protein labels.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

One embodiment of the invention provides a fluorescent probe and a method of preparing a fluorescent probe. The probe comprises a Sandercyanin moiety attached to a probe for detecting a specific target wherein, when excited, the probe emits a fluorescent signal. By "fluorescent," we mean the probe exhibits fluorescence.

By "Sandercyanin" or "nSFP" we mean the native blue fluorescent protein, preferably as set forth in SEQ ID NO: 1.

By "recombinant Sandercyanin" or "rSFP" we mean the isolated recombinant fluorescent protein set forth in SEQ ID NO: 2.

By "Sandercyanin moiety" we mean an amino acid sequence with at least 80% sequence identity to SEQ ID NOs:1 or 2. In some embodiments, Sandercyanin moiety also refers to an amino acid sequence with at least 90% sequence identity to SEQ ID NOs:1 or 2. In other embodiments, the Sandercyanin moiety has an amino acid sequence with at least 95% sequence identity to SEQ ID NOs:1 or 2.

In some embodiments the Sandercyanin moiety may comprise a fragment of the Sandercyanin protein. By "fragment" we mean a portion of the native or recombinant Sandercyanin protein that retains at least 75%, in some embodiments 95%, of the fluorescent properties of the Sandercyanin protein. There are 15 amino acid residues which are positioned at a distance of 4 Å from the chromophore that are required for the observed fluorescence properties of the protein, including, amino acids D47, F55, S61, T62, A63, N77, R78, E79, S87, H108, Y116, S131, Y142, L135 and A137.

By "target" we mean any biomolecule or non-biomolecule. By "biomolecule" we mean any biological molecules known to the art, including, without limitation, antibodies; proteins, in particular proteins recognized by particular antibodies; receptors; enzymes or other ligands; nucleic acids (e.g., single or double stranded DNA, cDNA, mRNA, cRNA, rRNA, tRNA, etc.); various sugars and polysaccharides; lectins; and the like.

By "probe" we mean any probe known to the art, including, for example and without limitation, antibodies, proteins and enzymes.

In other embodiments, the invention provides a method of using a fluorescent probe, comprising the steps of obtaining the fluorescent probe as described above, exposing the probe to a desired target, and exposing the probe and target to light having a wavelength ranging from about 350-690 nm, wherein the fluorescent probe fluoresces.

In other embodiments, the invention provides a fluorescent labeled marker for detection of a target, the marker comprising a label selected from the group consisting of Sandercyanin fluorescent protein and a fluorescent variant thereof, and a ligand configured to bind to the target.

By "fluorescent labeled" we mean derivatizing a molecule with a fluorescent material.

By "ligand" we mean any ligand known to the art, including, for example and without limitation, a nucleic acid probe, an antibody, a hapten conjugate, biotin, avidin and streptavidin.

In other embodiments, the invention provides a method for detecting a target comprising: providing a fluorescent-labeled ligand which incorporates a label selected from the group consisting of Sandercyanin fluorescent protein and a fluorescent variant thereof, and a ligand for binding the target; contacting the target with the labeled ligand; allowing the labeled ligand to bind to the target; subjecting the labeled ligand and target to light having a wavelength which excites the label; and observing the locus of fluorescence.

The fluorescence may be measured by any technique known to the art, including for instance, flow cytometry. By "flow cytometry" or "FACS" we mean a technique for examining the physical and chemical properties of particles or cells suspended in a stream of fluid, through optical and electronic detection devices.

In other embodiments, the invention provides a method for producing an isolated recombinant protein comprising introducing DNA encoding an exogenous protein into the organism, culturing the organism in an enclosed system, harvesting the organism, and isolating the recombinant protein from the organism, wherein the recombinant protein is Sandercyanin fluorescent protein. The DNA may contain a promoter that is functional in the organism.

By "isolated" we mean a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

By "recombinant" we mean a protein that has been manipulated in vitro, e.g., using recombinant DNA technology to introduce changes to the viral genome.

Advantages of the Sandercyanin Protein.

The Sandercyanin protein offers many advantages over conventional fluorescent proteins.

First, it expresses efficiently, without toxicity and its fluorescence is at least bright enough to provide sufficient signal above autofluorescence.

Second, the photostability of the Sandercyanin protein is compatible use as a fluorescent protein. For instance, the isolated Sandercyanin protein of the present invention is very stable protein, making it easy to work with in a variety of ways. Further, the smaller size of this protein enables it to be easily manipulated for use.

Third, the Sandercyanin protein may be expressed as a fusion to another protein, and will remain fluorescent and should not interfere with the protein's folding, cleavage and maturation processes. In addition, folding and maturation of the Sandercyanin protein is not impaired by its fused partner(s).

Fourth, the Sandercyanin protein's sensitivity to environmental changes is also compatible with its intended use as a fluorescent protein.

Fifth, the large Stokes Shift of the Sandercyanin protein provides greatly improved detectability. For instance, the protein's emission in red emits very little scattering, making the Sandercyanin protein very well suited for, among other things, deep tissue imaging.

In addition, the protein acts as a non-covalent ligand, making it easy to regenerate after photo-bleaching. The protein's ability to turn on when required by adding the ligand (especially in extracellular applications) provides a huge advantage over conventional fluorescent proteins.

The Sandercyanin protein's excitation and emission wavelength, number of spectral peaks, quantum efficiency, extinction coefficient, Stokes shift, degree of aggregation and oligomerization, time to maturation and ability to participate in fluorescence resonance energy transfer all support these advantages.

Finally, the protein of the present invention allows for the efficient and cost-effective methods to engineer from available crystal structure.

Commercial Applications of the Sandercyanin Protein.

Biomarker. Uses of the various Sandercyanin-labeled biomolecules will be readily apparent to one of skill in the art. Thus, for example, Sandercyanin-labeled nucleic acids can be used as probes to specifically detect and/or quantify the presence of the complementary nucleic acid in, for example, a Southern blot. In various embodiments, the Sandercyanin-labeled biomolecules can be expressed in fusion with a heterologous protein and in this context can act as a reporter molecule (e.g., when contacted with a (native or exogenous) bilin) to identify gene activations, protein expression, and/or protein localization within a cell. Similarly, the Sandercyanin-labeled biomolecules can act to identify particular cell populations in cell sorting procedures.

In other embodiments, the Sandercyanin protein can be attached to non-biological molecules or articles. By "non-biological molecule or articles" we mean synthetic compounds or medical devices, implants and the like. Thus, for example and without limitation where it is desired to associate a specific medical device or implant with a particular manufacturer, distributor, or supplier, the Sandercyanin label, or a fragment of the protein label, can be attached to the subject article. Later "development" (e.g., by addition of a second component such as bilin or apoprotein) and exposure to an appropriate light source will provide a fluorescent signal identifying the article as one from a source of such labeled articles.

In still other embodiments, the Sandercyanin protein of this invention can be used as in vitro or in vivo labels in a manner analogous to the use of Green Fluorescent Protein (GFP). This typically involves transfecting a cell with a nucleic acid encoding an apoprotein in such a manner that the cell expresses the apoprotein (e.g., the nucleic acid is a component of an expression cassette). When the apoprotein is contacted with the appropriate bilin, supplied either exogenously or produced endogenously, the phytofluor (fluorescent adduct) self assembles and thereby produces a fluorescent marker. Uses of such a marker are well known to those of skill in the art (see, e.g., U.S. Pat. No. 5,491,084 which describes uses of GFP).

In one preferred embodiment, the Sandercyanin protein can be used as a marker to identify transfected cells. Based on the disclosure provided herein, one of skill will readily appreciate that there are numerous other uses to which the fluorescent protein of this invention can be applied.

For instance, red fluorescence (NIR range) of the Sandercyanin fluorescent protein makes it a promising in vivo marker for deep tissue imaging. Because biliverdin is present in mammalian cells as a product of heme-degradation, the intrinsic fluorescence can be observed expressing the Sandercyanin fluorescent protein tagged to a known protein. Further, because biliverdin is a non-covalent chromophore, it will replenish fluorescence after photo-bleaching on adding external biliverdin.

By "polypeptide", "peptide" and "protein", we mean a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

Fluorescent Probe. In another embodiment, the Sandercyanin protein can be used for probing protein-protein interactions. Protein-protein interaction between two proteins of interest (e.g., protein X and protein Y) is identified following their co-expression as translational fusions with the Sandercyanin protein in constructs 1 (donor) and 2 (acceptor) using fluorescence energy transfer from the shorter wavelength-absorbing donor species to the longer wavelength-absorbing acceptor species. In a preferred embodiment, the fluorescent phytochrome species are selected to have good spectral overlap. Proximity caused by the protein-protein interaction between the translational fused proteins X and Y will then permit fluorescence energy transfer thereby providing an indication of proximity between protein X and protein Y.

In an illustrative application, a yeast or E. coli strain containing donor construct 1, engineered to produce a fluorescent chimeric protein "bait" with a known cDNA sequence, is co-transformed, simultaneously or sequentially, with a "prey" cDNA library (i.e., plasmid or phage). The "prey" cDNA library is constructed using acceptor construct 2 for expression of apoprotein-protein fusions which yield fluorescent tagged protein products in the presence of the correct bilin. Co-transformation events that express "prey" proteins in the library that interact with the expressed "bait" polypeptide can be identified by illuminating the shorter wavelength absorbing donor phytofluor species and viewing emission from the longer wavelength acceptor phytofluor emitting species. Actinic illumination for this screen can either be obtained with a quartz halogen projector lamp filtered through narrow bandpass filters or with a laser source and fluorescent detection of colonies using digital imaging technology (Arkin et al. (1990)). Fluorescent activated cell sorting (FACS) can also be used to identify cells co-expressing interacting donor and acceptor proteins.

In another illustrative application, chimeric apoprotein-protein X cDNA (where protein X is any protein of interest) are expressed in transgenic eukaryotes (yeast, plants, Drosophila, etc.) in order to study the subcellular localization of protein X in situ. Following feeding of exogenous bilin, subcellular localization can be performed using fluorescence microscopy (e.g., laser confocal microscopy).

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Collecting the Sandercyanin Protein

Study Sites. McKim Lake (50° 54' N, 92° 45' W) is located within the Papaonga River system of northwestern Ontario, Canada, (FIG. 1) and is known to support sympatric populations of blue and yellow walleye (Yu et al. 2008). All Ontario walleye were sampled from McKim Lake (surface area of 313 hectares and a maximum depth of 13.7 m). Control samples for walleye that represent the typical yellow color form and do not exhibit blue color in their mucus at this time were obtained from Lake Erie near Port Clinton, Ohio (41° 30' N, 82° 56' W).

Fish Sampling. Fish in McKim Lake and Lake Erie were sampled via angling. We classified fish in two color categories: blue or yellow. Although both color forms contained Sandercyanin in their skin mucus, walleye were classified as blue only if no yellow pigment was present in their skin. In McKim Lake, fish were sampled a total of 22 times between the months of March and October over a 6 year period, 2006-2011 (Table 1). For each fish caught, weight and total length at capture (+/−1 mm) were recorded and sex was determined, whenever possible, by gonad examination. A total of 305 walleye (blue: N=82, gold: N=223) were sampled from McKim Lake (Table 1).

TABLE 1

Sample dates for histological work from 2008-2011. Tissue samples were obtained from 2 fish on each sample date reported. Samples from McKim Lake always included one blue and one yellow color form. Samples from Lake Erie always included two walleye of the typical yellow coloration.

| Sample Date | Color Form | Source Lake | ID# |
|---|---|---|---|
| May 27, 2008 | Blue | McKim | BWM10 |
| May 27, 2008 | Yellow | McKim | YWM11 |
| Aug. 08, 2008 | Blue | McKim | BWM13 |
| Aug. 08, 2008 | Yellow | McKim | YWM12 |
| Aug. 09, 2009 | Blue | McKim | BWM16 |
| Aug. 09, 2009 | Yellow | McKim | YWM17 |
| Mar. 21, 2010 | Blue | McKim | BWM20 |
| Mar. 21, 2010 | Yellow | McKim | YWM21 |
| Jun. 10, 2010 | Blue | McKim | BWM22 |
| Jun. 10, 2010 | Yellow | McKim | YWM23 |
| Aug. 26, 2010 | Blue | McKim | BWM27 |
| Aug. 26, 2010 | Yellow | McKim | YWM28 |
| Jun. 12, 2011 | Blue | McKim | BWM33 |
| Jun. 12, 2011 | Yellow | McKim | YWM32 |

TABLE 1-continued

Sample dates for histological work from 2008-2011. Tissue samples were obtained from 2 fish on each sample date reported. Samples from McKim Lake always included one blue and one yellow color form. Samples from Lake Erie always included two walleye of the typical yellow coloration.

| Sample Date | Color Form | Source Lake | ID# |
|---|---|---|---|
| Aug. 24, 2011 | Blue | McKim | BWM37 |
| Aug. 24, 2011 | Yellow | McKim | YWM38 |
| Jul. 29, 2010 | Yellow | Erie | YWE25 |
| Jul. 29, 2010 | Yellow | Erie | YWE26 |
| Aug. 03, 2011 | Yellow | Erie | YWE35 |
| Aug. 03, 2011 | Yellow | Erie | YWE36 |

Histology Samples. Histological examination of the epidermis of walleye was done in an effort to determine which cells were producing and/or storing Sandercyanin. Study tissue was obtained from freshly caught specimens by removing the third dorsal spine, together with about 10 mm of underlying tissue. All tissue samples were immediately fixed in the field in neutral buffered, 10% formalin solution. Twenty fish total were sampled for histological study; 8 blue walleye from McKim Lake in Canada with Sandercyanin, 8 yellow walleye from McKim Lake in Canada with Sandercyanin and 4 walleye from Lake Erie with no Sandercyanin (Table 1). Canadian samples were taken during the months of March-August over a period of 4 years (2008-2011). Lake Erie samples were taken in late July over a period of 2 years (2010-2011). All histological work and microphotography was performed at the National Fish Health Research Laboratory in Kearneysville, W. Va. Tissues were routinely processed (Luna, 1992), embedded in paraffin, sectioned at 5 um. Three different stains were used to visually distinguish the location of cells containing Sandercyanin: Periodic Acid Schiff (PAS), Masson's Trichrome (TR) and Alcian Blue (AB).

Mucus Samples. Gross anatomical location of Sandercyanin on the fish was determined by visual observation and photography in the field as well as macrophotography of fresh specimens in the lab using a dissecting microscope fitted with a digital camera. We collected mucus from individual walleye by scraping the epidermal surface of each fish in an anterior to posterior direction using a knife (Yu et al. 2007). Mucus was removed from the entire surface of the fish excluding the head and starting immediately posterior to the operculum, including both sides of each fish. All mucus removed from individual walleye was added to a vial containing approximately 20 ml of lake water. Successive scrapings were performed as needed on an individual basis until additional scrapings yielded no new mucus deposits on the knife blade. Care was taken to avoid removing scales and the deeper dermis layer. Time devoted to individual mucus samples varied based on the amount of mucus present and the size of individual fish sampled. Mucus samples were stored at 0° C. until analyzed.

To prepare the frozen samples for spectroscopic analysis in the lab we first thawed the samples and then noted the total volume (ml) of each sample. We homogenized the sample (shook it up) and then obtained a 1.0 ml subsample using a micropipette. We centrifuged the 1 ml sample for 15 minutes at 16,000 rpm, and then removed a 0.25 ml subsample from the supernate for final absorbance analysis. We used a Versamax micro plate spectrophotometer (Molecular Devices, Sunnyvale, Calif.) to read absorbance at 633 nm, the absorbance maxima reported for Sandercyanin (Yu et al. 2007). The bluer the sample, the higher the absorbance. Differences in total sample volume existed due to variation in water volume added to sample vials in the field. However, since absorbance readings were demonstrated to be directly proportional to the amount of blue pigment in the supernate, we multiplied the absorbance reading by the final sample volume (absorbance*volume) to represent the total amount of Sandercyanin present in each sample. As such, the product of absorbance*volume was used in all subsequent statistical analyses and figures.

Results.

General Morphology. Blue colored walleye contained no yellow pigment in their skin and appeared steel gray in color (FIG. 2). The blue morphs had a white belly. Sandercyanin was present in the mucus of both blue and yellow morphotypes of walleye from McKim Lake; however, blue pigmentation was more apparent in the blue color forms as their fins were translucent from lack of gold pigment (FIG. 3). Both dorsal fins and the upper caudal fin particularly exhibited blue color. Based on our visual observations it was clear that Sandercyanin was present in highest abundance on the dorsal surface of fish above the lateral line (FIG. 4).

Microscopic examination, using a dissecting microscope, revealed a distinct blue line containing Sandercyanin immediately adjacent to, and running parallel to each spine in both dorsal fins and in the upper part of the caudal fin (FIG. 5). Pectoral fins also contained blue color but no blue color was noted in either pelvic or anal fins. Lines of the blue protein were observed directly adjacent to blood vessels running the length of each dorsal fin spine and located in a longitudinal groove within the structure of each spine (FIG. 6). Blue coloration was also observed surrounding the sclera of the eye. Closer microscopic examination of the mucus using a compound scope showed the blue protein to be contained within membrane-bounded structures in the epidermis and in the skin mucus (FIGS. 7, 8). No nuclei were observed in these blue structures.

Histological Location of Cells Containing Sandercyanin. All three histological stains, used in the study, showed the presence of a novel group of secretory cells, containing Sandercyanin, and located in the epidermis immediately below superficial mucus cells, but above the basement membrane of the epithelium. Comparison of cross sections of walleye epidermis from Canada and Lake Erie are shown in three microphotographs. Epidermal cross-sections were compared using PAS (FIG. 9), Masson's Trichrome (FIG. 10) and Alcian Blue (FIG. 11). The Canadian fish from McKim Lake all showed cells containing Sandercyanin, whereas, the control walleye from Lake Erie demonstrated no such cells. The pigment containing cells were oval in shape and approximately 60 microns in diameter. We propose the name "Sander Cells" for this newly identified line of secretory cells containing Sandercyanin.

Abundance of Pigment Containing Cells Appeared to Vary by Season. Histological sections of walleye from McKim Lake captured in March of 2010 were qualitatively compared to those from walleye captured in August of 2010. A visual difference between these slides was observed with the August samples displaying an apparent higher concentration of Sandercyanin within their pigment containing cells than walleye captured in March (FIG. 12). We observed similar differences in other years (2008 & 2011) where samples across multiple seasons were obtained.

Seasonal Production of Sandercyanin. Absorbance readings were done for mucus samples collected from 305 walleye in McKim Lake during 22 sample dates representing 8 different months across a 6-year period (Table 2).

TABLE 2

Mean absorbance of walleye mucus at 633 nm.

| Date | Day | Mon | Year | N | Absorbance (mean ± SD) | | Volume (ml) (mean ± SD) | | Absorbance * Vol. (mean ± SD) | |
|---|---|---|---|---|---|---|---|---|---|---|
| Mar. 22, 2006 | 81 | 3 | 2006 | 15 | 0.0648 | 0.0269 | 26.3 | 4.9493 | 1.6570 | 0.6550 |
| May 26, 2006 | 146 | 5 | 2006 | 13 | 0.0720 | 0.0261 | 17.8 | 3.4119 | 1.2576 | 0.4262 |
| Jun. 26, 2006 | 177 | 6 | 2006 | 10 | 0.0589 | 0.0104 | 18.4 | 4.6952 | 1.0937 | 0.3811 |
| Aug. 26, 2006 | 238 | 8 | 2006 | 10 | 0.1732 | 0.0718 | 17.1 | 1.6633 | 2.9828 | 1.3329 |
| Oct. 5, 2006 | 278 | 10 | 2006 | 10 | 0.0521 | 0.0107 | 12.7 | 5.4579 | 0.6248 | 0.2047 |
| Mar. 19, 2007 | 78 | 3 | 2007 | 53 | 0.0772 | 0.0232 | 20.7 | 0.9605 | 1.5946 | 0.4812 |
| Jun. 23, 2007 | 174 | 6 | 2007 | 9 | 0.0876 | 0.0169 | 20.1 | 1.0541 | 1.7599 | 0.3422 |
| Jul. 25, 2007 | 206 | 7 | 2007 | 9 | 0.1101 | 0.0468 | 21.0 | 2.1213 | 2.3432 | 1.1126 |
| Aug. 25, 2007 | 237 | 8 | 2007 | 25 | 0.1376 | 0.0584 | 20.6 | 2.9563 | 2.8011 | 1.2062 |
| Sep. 21, 2007 | 264 | 9 | 2007 | 9 | 0.1387 | 0.0747 | 21.2 | 2.4889 | 3.0749 | 2.0285 |
| Jan. 28, 2008 | 28 | 1 | 2008 | 3 | 0.0686 | 0.0071 | 22.0 | 2.0000 | 1.5034 | 0.1401 |
| May 27, 2008 | 147 | 5 | 2008 | 12 | 0.0571 | 0.0096 | 20.9 | 1.7816 | 1.1951 | 0.2283 |
| Jun. 23, 2008 | 174 | 6 | 2008 | 12 | 0.0946 | 0.0471 | 18.7 | 1.7233 | 1.7473 | 0.8313 |
| Jul. 30, 2008 | 211 | 7 | 2008 | 11 | 0.1390 | 0.0490 | 19.7 | 1.3484 | 2.7570 | 1.0459 |
| Aug. 9, 2008 | 221 | 8 | 2008 | 32 | 0.1301 | 0.0451 | 20.7 | 0.7289 | 2.6946 | 0.9303 |
| Jun. 24, 2009 | 175 | 6 | 2009 | 9 | 0.0929 | 0.0349 | 18.6 | 1.0442 | 1.7137 | 0.6173 |
| Aug. 14, 2009 | 226 | 8 | 2009 | 20 | 0.1213 | 0.0518 | 20.1 | 0.6043 | 2.4606 | 1.1276 |
| Mar. 22, 2010 | 81 | 3 | 2010 | 10 | 0.0866 | 0.0370 | 18.9 | 1.4347 | 1.6076 | 0.5886 |
| Jun. 10, 2010 | 161 | 6 | 2010 | 10 | 0.0798 | 0.0315 | 17.8 | 3.4014 | 1.3627 | 0.4673 |
| Aug. 26, 2010 | 238 | 8 | 2010 | 4 | 0.2952 | 0.1454 | 18.3 | 1.7559 | 5.5045 | 3.1310 |
| Jun. 10, 2011 | 161 | 6 | 2011 | 10 | 0.1143 | 0.0788 | 17.9 | 1.2867 | 1.9878 | 1.2056 |
| Aug. 24, 2011 | 236 | 8 | 2011 | 9 | 0.2039 | 0.1018 | 19.3 | 2.2776 | 3.8437 | 1.6798 |

Absorbance varied significantly by month and fish length ($p<0.0001$, Table 3).

TABLE 3

ANOVA for effect month, color (blue and gold) and total length on the amount of Sandercyanin present in walleye mucus (represented by absorbance * volume).

| Source of Variation | Sum of Squares | F Ratio | Prob > F |
|---|---|---|---|
| Month | 38.2936 | 43.806 | <0.0001 |
| Color | 0.34791 | 2.786 | 0.0962 |
| Log(Length) | 5.88662 | 47.138 | <0.0001 |
| Month * Color * Length | 2.49466 | 2.854 | 0.0068 |

A plot of mean absorbance at 633 nm times sample volume across all 22 sample dates is shown in FIG. 13. For each of the six sample years, absorbance peaked near the end of August, indicating that production of Sandercyanin is seasonal and is greatest at that time of year.

Seasonal differences between color morphs were tested using ANOVA by comparing spring (months 3, 5 & 6) and summer (months 7-9), Table 4.

TABLE 4

ANOVA for effect of season (spring and summer) and color (blue and gold) on the amount of Sandercyanin present in walleye mucus (represented by absorbance * volume).
Spring includes the months of March, May and June.
Summer includes the months of July, August and September.

| Source of Variation | DF | Sum of Squares | F Ratio | Prob > F |
|---|---|---|---|---|
| Season | 1 | 9763.907 | 92.421 | <0.001 |
| Color | 1 | 705.530 | 6.678 | 0.0103 |
| Season * Color | 1 | 62.696 | 0.594 | 0.4417 |

Examination of the least square means from the two-way ANOVA indicated that both color forms contain lower levels of Sandercyanin in the spring, but the yellow color form demonstrated a larger increase in concentration of Sandercyanin in the summer months compared to blue individuals (Table 5).

TABLE 5

Least square means and standard errors based on a two-way ANOVA testing for the effect of season (spring and summer) and color (blue and gold) on the amount of Sandercyanin (represented by absorbance * volume). March, May and June were classified as spring; summer included the months of July, August and September.

| Level | Lst Sq. Mean | Std. Error |
|---|---|---|
| Blue, Spring | 13.6569 | 1.6252 |
| Blue, Summer | 25.6266 | 1.6252 |
| Gold, Spring | 16.1121 | 0.9268 |
| Gold, Summer | 30.1671 | 1.0895 |

Yellow color forms exhibited a higher absorbance in their mucus compared to blue walleye (FIG. 14, p=0.0103). Seasonal differences were confirmed with significantly higher levels of Sandercyanin present in mucus during the summer compared to spring months (p<0.0001) in both color forms. The interaction between color and season was not significant (p=0.4417).

Discussion.

Figure 19:
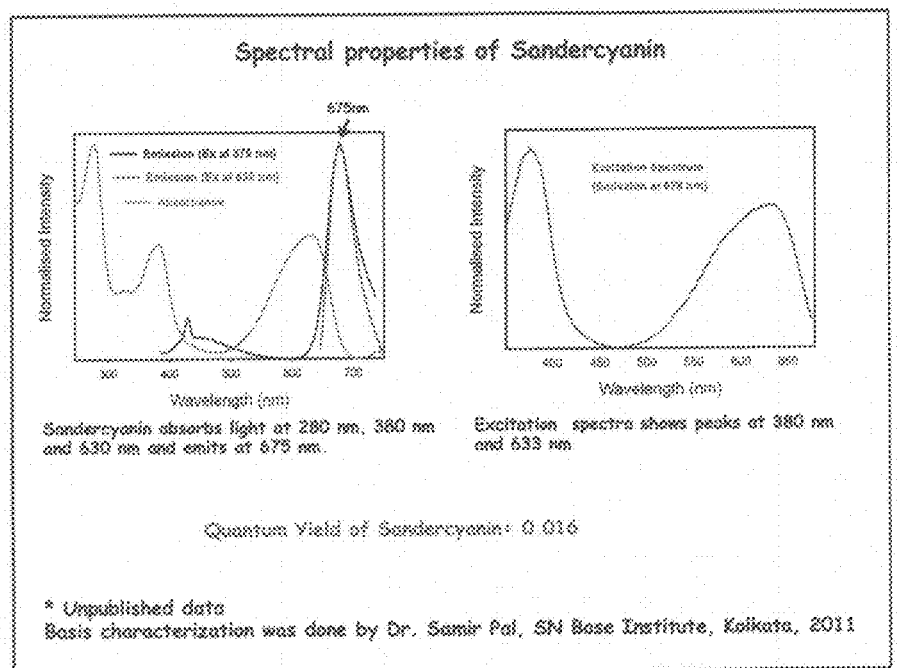
FIG. 19 shows the spectral properties of the Sandercyanin protein.
Figure 20:
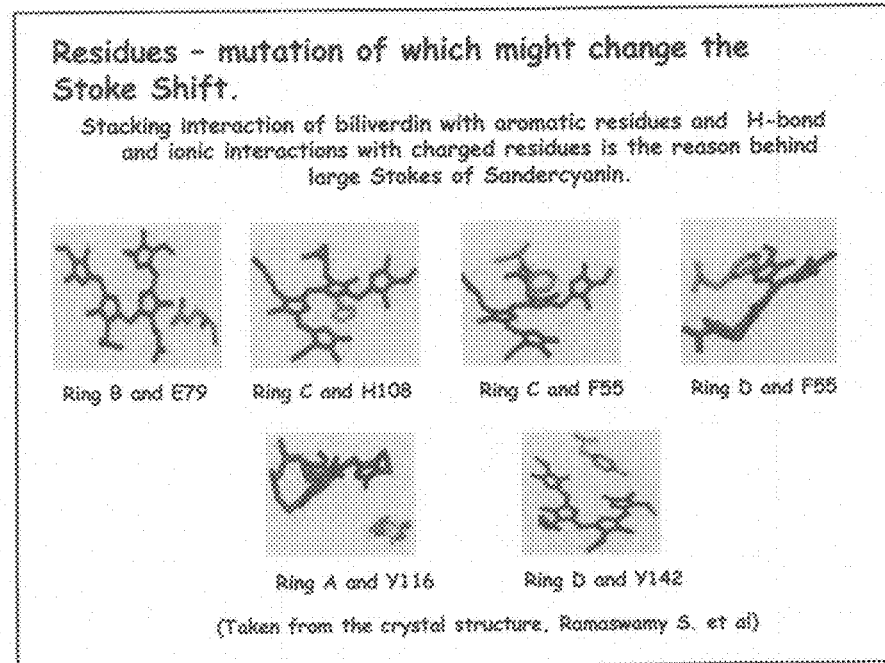
FIG. 20 shows protein residues which may impact the stoke shift.
Figure 21:
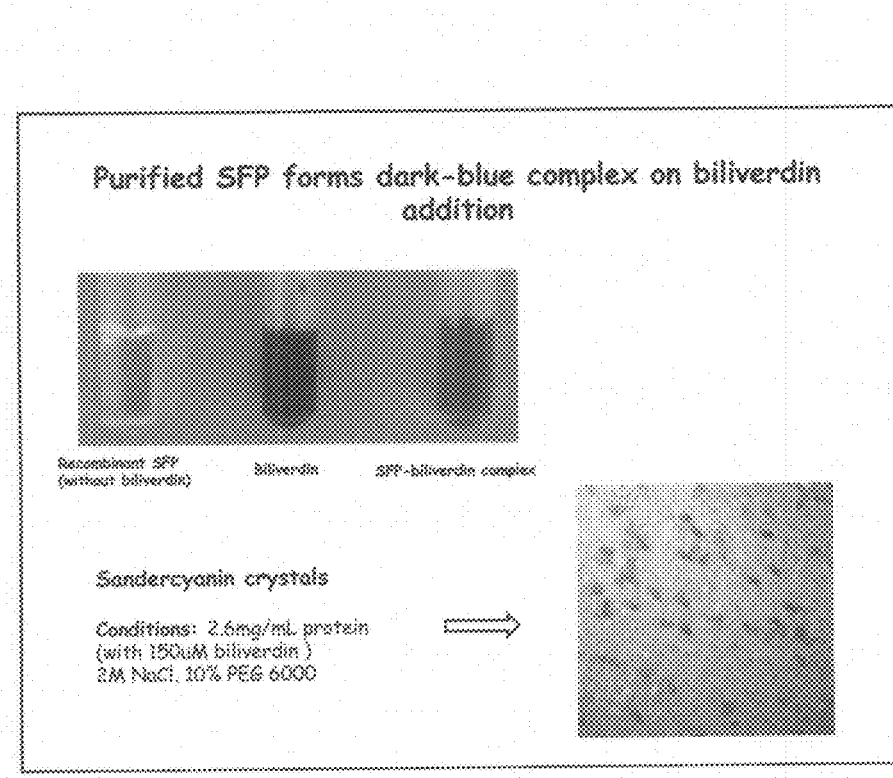
FIG. 21 illustrates how purified Sandercyanin protein reacts on contact with biliverdin.
Figure 22:
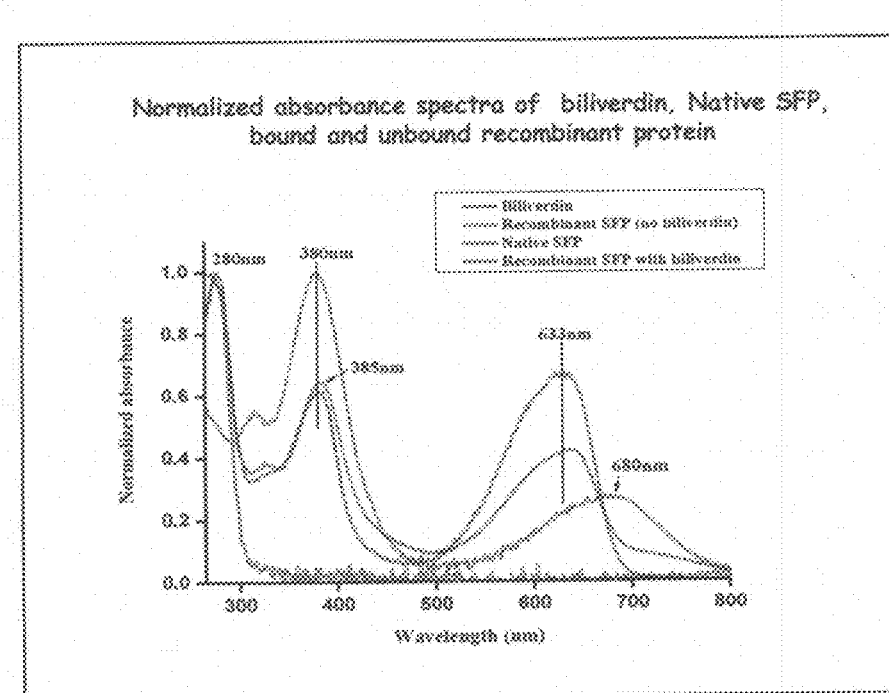
FIG. 22 compares the normalized absorbance spectra of biliverdin, Native Sandercyanin protein, bound and unbound recombinant Sandercyanin protein.
Figure 25:
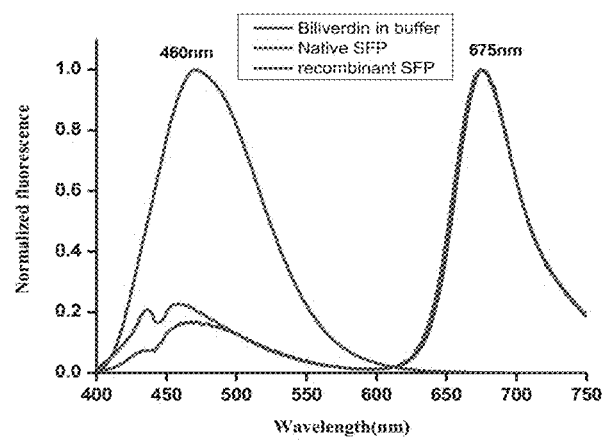
FIG. 25 illustrates how biliverdin emission changes significantly on binding to Sandercyanin protein.
Figure 26:
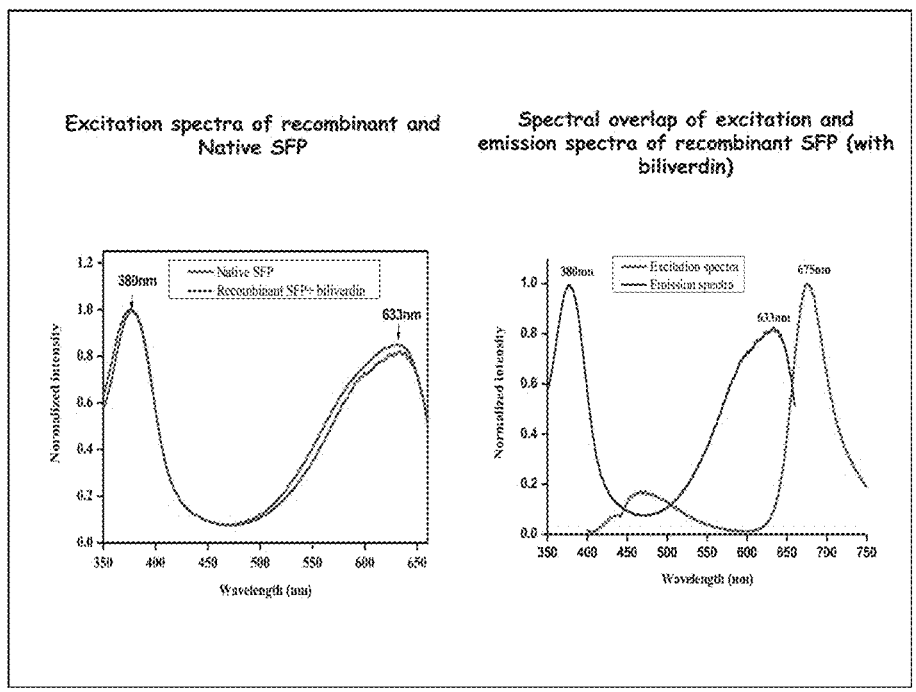
FIG. 26 shows the Excitation spectra of recombinant and native Sandercyanin protein and Spectral overlap of excitation and emission spectra of recombinant SFP (with biliverdin).
Figure 27:
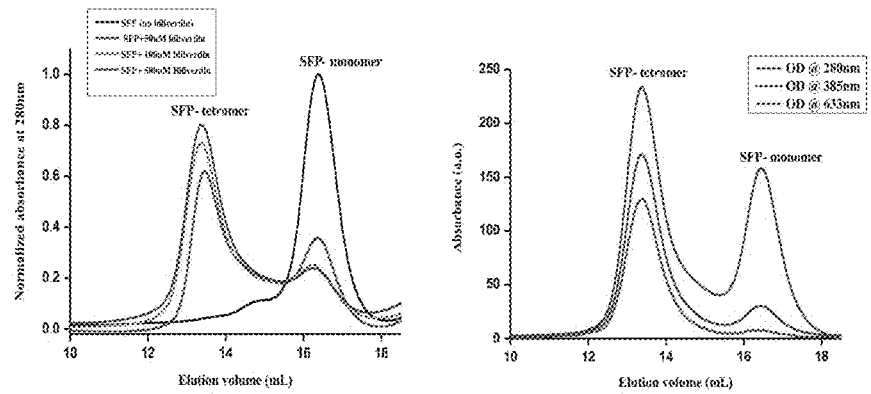
FIG. 27 illustrates the biliverdin-driven oligomerization of Sandercyanin protein.
Figure 28:
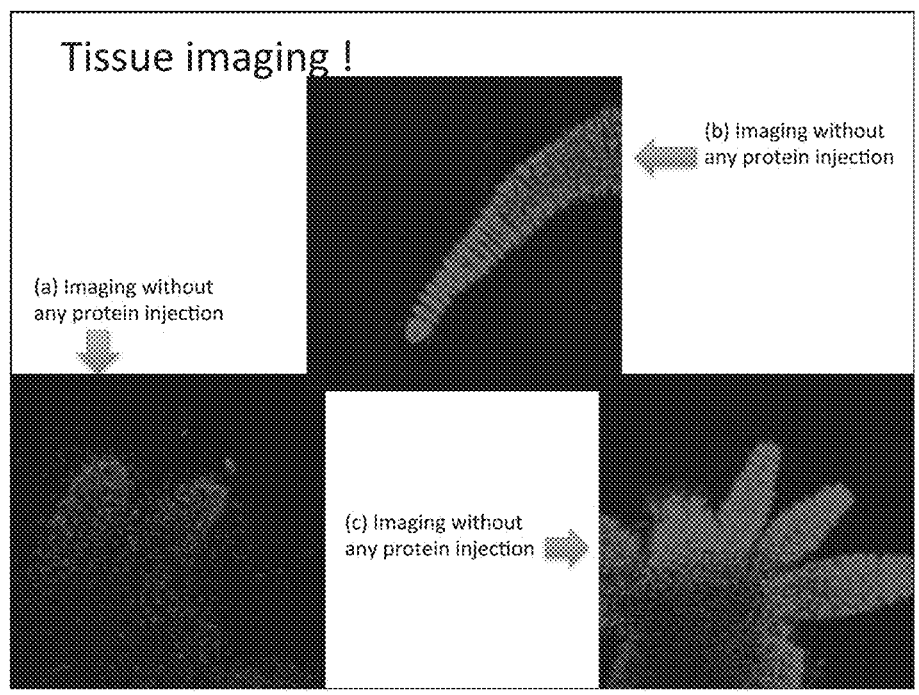
FIG. 28 shows tissue imaging without Sandercyanin protein.
Figure 29:
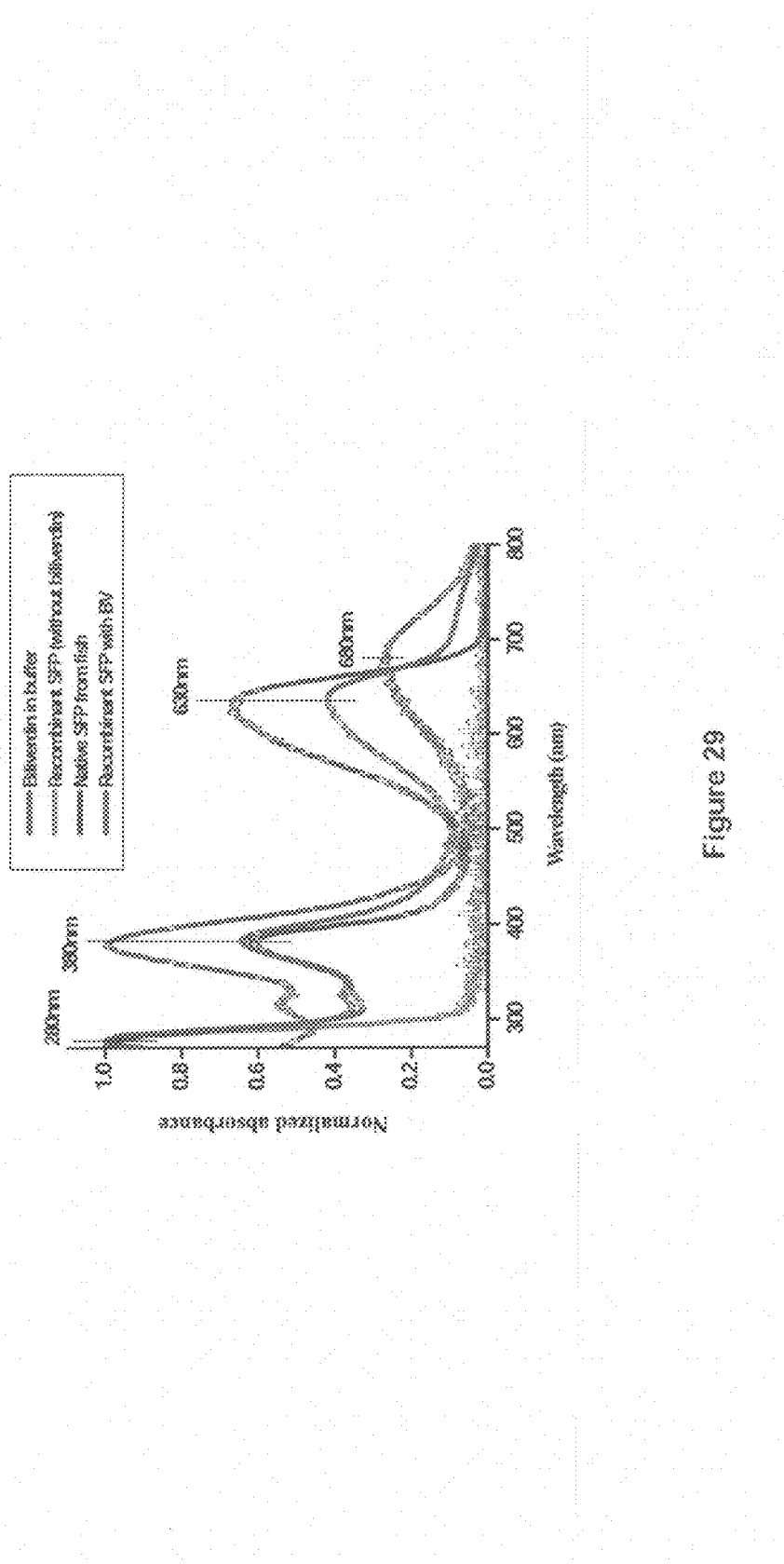
FIG. 29 compares the normalized absorbance spectra of free biliverdin, native Sandercyanin protein (isolated from fish) with biliverdin, free and biliverdin liganded recombinant Sandercyanin protein.
Figure 30:
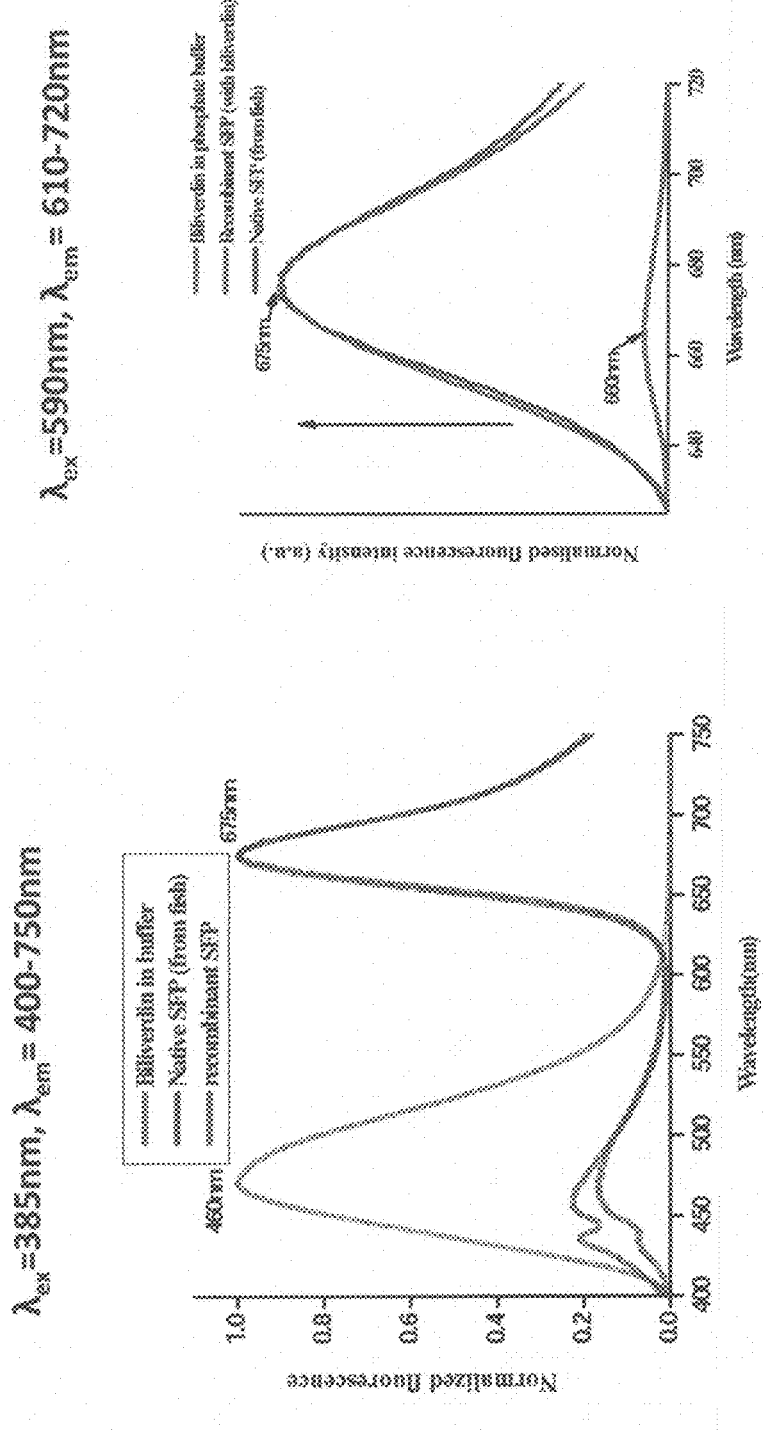
FIG. 30 compares the fluorescence spectra of recombinant Sandercyanin fluorescent protein (rSFP) and native Sandercyanin fluorescent protein (nSFP).
Figure 32:
FIG. 32 illustrates how native Sandercyanin fluorescent protein (nSFP) can show fluorescence when injected.

We have located and described what appears to be a new secretory cell within the epidermis of both blue and yellow walleye in McKim Lake, Ontario. We believe these cells store, and likely produce, the Sandercyanin protein of SEQ ID NO: 1. We propose the name "Sander Cells" for this previously undescribed line of unicellular epidermal secretory cells. Sander cells are completely absent in Lake Erie walleye, where blue colored mucus is not generally observed. Furthermore, histological changes are seen in these secretory cells between seasons in samples from McKim Lake. The increase in the intensity of stain within these secretory cells from spring to summer likely coincides with seasonal increases in the production of Sandercyanin documented herein (FIGS. 15-33).

Proliferation of Sander cells in the dorsal epidermis of walleye from McKim Lake is consistent with conventional observations of epidermal secretory cells, which found increased production of alarm cells in razorback suckers, *Xyrauchen texanus*, exposed to UVB radiation in the laboratory (Blazer et al. 1997) and suggested that epidermal alarm substance cells (ASC) functioned in fish defense against pathogens, parasites and UVB radiation (Chivers et al. 2007). The histology of ASCs is very similar to the histology of Sander cells reported here in size, shape and location within the epidermis. However, ASCs are nucleated, whereas the Sander cells we observed had no visible nucleus.

The presence of a colored pigment in the mucus of fish is highly unusual; color is generally confined within the skin of fish (Leclercq et al. 2010). Other blue-colored pigments have been reported in fish, but these have been restricted to blood components. Fang (1985) reported a blue-green color in the blood serum of the woolly sculpin (*Clinocottus analis*) and Gagnon (2006) described a blue color in the blood of the blue throated wrasse (*Notolabrus tetricus*). Like Sandercyanin, both pigments were related to the presence of biliverdin. Blue color has been reported in the mucus of *Odontosyllis phosphorea*, a marine annelid worm (Deheyn and Latz 2009). To our knowledge, this is the first report of color within free-floating membrane-bounded structures in the mucus of any fish.

Production of Sandercyanin in fin membranes near blood vessels in dorsal spines is consistent with the possible excretion of excess biliverdin from fish blood into the mucus. Sandercyanin is classified as a lipocalin (Yu et al. 2007), a group of proteins known to function in transport of small hydrophobic ligands, such as biliverdin (Flower 1996). Biliverdin is produced by the breakdown of heme in blood (Abraham and Kappas 2008). The breakdown of heme and conversion to biliverdin can be triggered by exposure to UV radiation (Allanson and Reeve 2005). Walleye from McKim Lake appear to be producing an excess of biliverdin that is excreted in their skin and incorporated into Sandercyanin within Sander cells. The observation of pigment containing cells around the sclera of the walleye eye is interesting. Retinol binding protein is also a lipocalin and may be binding biliverdin as well as retinol.

UVB radiation (280-320 nm) can penetrate the water column and has recently increased at the earth's surface due to ozone depletion caused by increased input of chlorofluorocarbons to the atmosphere (Kerr and McElroy 1993). It is well documented that UV radiation has damaging effects on many biological molecules including DNA and proteins in fish (reviewed in Zagarese and Williamson 2001), although the mechanisms of UV-protection in fish remain largely undescribed (Leclercq et al. 2010). Many of the secretory products of the epidermis of teleost fish are protective (reviewed in Whitear 1986). Although we have no direct evidence of cause and effect, multiple observations suggest the ecological function of Sandercyanin may be related to photo-protection from UV radiation.

We have demonstrated histologically that Sandercyanin is contained in secretory cells in the epidermis of walleye. The pigment contains biliverdin (Yu et al. 2007), a known tissue-protectant (Bellner et al. 2011). We further observed Sandercyanin to be located disproportionately on the dorsal surface of the fish, the area most exposed to UV radiation. The secretory cells we describe here may be important in protection against UV damage, through increased production of Sandercyanin that may function as a natural sunscreen.

The absorption spectrum of Sandercyanin peaks at 280, 383 and 633 nm (Yu et al. 2007). This includes absorption in both the UVA range (320-400 nm) and near UVB range (290-320 nm). By absorbing wavelengths throughout the UV spectrum, Sandercyanin may function similar to melanin that acts as an optical barrier and prevents the penetration of UV into the underlying tissue (Kollias et al. 1991). Many proteins unrelated to photo-protection have an absorbance peak at or near 280 nm (Whitaker and Granum 1980). Still, Fabacher and Little (1995) described an unknown skin component with an absorption maximum of 292 nm and demonstrated a strong relationship between the amount of this substance and the period of time it took to develop sunburn in several freshwater fish species. Sandercyanin in the mucus of walleye could block UV radiation from reaching critical macromolecules in the skin and deeper tissues.

Photo-protective compounds have been commonly found in the mucus of tropical reef fish which are naturally exposed to high levels of UV radiation (Zamzow and Losey 2002). In particular, mycosporine-like amino acids have been shown to absorb ultraviolet radiation across an array of coral reef organisms (reviewed in Dunlap and Shick 1998). Sandercyanin may provide similar protection to walleye at high latitudes in North America that are exposed to increased levels of UV radiation as a result of arctic ozone depletion which is increasing (Manney et al. 2011). It is important to note that production of Sandercyanin in walleye is confined to only northern latitudes at this time, basically, above the USA-Canadian Boarder. However, we have personally observed a progressive increase in the southern distribution of Sandercyanin in walleye during the 14 years of this study and would expect that trend to continue if the ozone hole over the North Pole continues to increase in size.

We have demonstrated here that the production of Sandercyanin increases from spring to summer months and hypothesized that this increase may be attributed to a seasonal increase in UV exposure. Hansson (2004) measured photosynthetically active radiation at various water depths in six lakes in southern Sweden (55.7° N, 13.5° E). The study indicated the UV threat was considerably higher during summer than during spring, fall and winter, with incident UV radiation levels being highest in July and August. Although we did not quantify UV radiation levels in the current study, McKim Lake is located at a similar latitude as southern Sweden and there is likely a similar increase in incident UV radiation during the summer months in Ontario, Canada. Future research is needed to quantify the relationship between increased UV exposure and production of Sandercyanin.

We further have demonstrated here that yellow color forms of walleye produce more Sandercyanin than their blue counterparts throughout the year and this difference increases between spring and summer seasons. One of the authors of this paper, Schmitz (2011) has provided evidence that suggests blue and yellow walleye have diverged morphologically based on a trophic polymorphism. Yellow walleye appear to be morphologically specialized to feed in near-shore littoral areas, where blue forms may feed more efficiently on benthic invertebrates and likely forage in relatively deeper water compared to yellow walleye. Based on the foraging niches described between these color forms, it is likely that yellow walleye in Ontario spend more time in shallow water and may be exposed to higher levels of UV radiation. The fact that yellow walleye show an increase in the production of Sandercyanin over blue color forms further indicates that production of Sandercyanin is related to UV exposure and that the protein may function as a photo-protectant.

In calanoid copepods, red carotenoids have been shown to be a UV protective pigment (Hansson and Hylander 2009). Being intensely colored, however, also increases the risk of mortality through predation from visual hunters such as fish. In copepods there is a trade-off between being pigmented and protected against UV radiation, but at the same time being vulnerable to predation. Unlike the vivid coloration of copepods, the blue color of Sandercyanin may function to promote cryptic coloration in walleye by covering conspicuous chromatophores in yellow walleye. Foraging success of northern pike (*Esox lucius*), the most common predator of walleye in Canada, is largely dependent on prey pigmentation (Jonsson et al. 2011) and walleye with Sandercyanin in their mucus may be more cryptically colored. If Sandercyanin functions in UV protection and/or cryptic coloration, the ability to produce this blue pigment would result in higher fitness for these individuals.

The nature and extent of the relationship between UV exposure and the production of Sandercyanin may become a fascinating area of future research. We recommend that future studies include more fine-scale analysis of seasonal changes in the abundance of pigment containing cells (Sander cells). Methods have already been described for quantifying the number of superficial goblet cells (Pickering and Fletcher 1987). Furthermore, laboratory experiments could subject walleye to specific UV radiation treatments. These experiments would provide direct evidence of cause and effect between UV exposure and production of Sandercyanin. The presence or absence of sunburn under various UV treatments (Fabacher and Little 1996) could provide direct evidence of the function of Sandercyanin as a natural sunscreen. We also suggest that further studies be conducted concerning the global distribution of Sandercyanin in percid species with specific reference to our hypothesized increased southern movement of the pigment as ozone depletion in the upper atmosphere changes. Also of future research interest may be the presence of a large, novel, horseshoe-shaped organelle-like structure within each pigment containing cell that likely aids in production of Sandercyanin.

Example 2

Purification of the Sandercyanin Protein

In this example, the inventors describe how to isolate and purify the native Sandercyanin protein according to SEQ ID NO: 1 of the present invention.

SEQ ID NO: 1. Sequence of native Sandercyanin protein (from fish, without signal peptide).

(SEQ ID NO: 1)
QFIKPGRCPKPAVQEDFDAARYLGVWYDIQRLPNKFQKGECATATYSLSP

GVGFSVFNRERLANGTIKSVIGSAIAEDPCEPAKLQFFHENAAPVPYWVL

STDYDNYALVYSCINLGASHAAYASIVSRQPTLPEETIKKLQGTMSSFGV

GVDTLLTTNQDAAYCSAMNQ.

All chromatographic procedures were performed in a cold room at 4° C. using an automated fast protein chromatography system (Bio-Rad Laboratories, Hercules, Calif.). Chromatography columns and column supports were from Amersham Biosciences, Piscataway, N.J., except for ceramic hydroxyapatite, which was obtained from Bio-Rad Laboratories.

The diluted mucus solution (110 ml) from blue walleye forms was centrifuged at 15,800 g for 15 min and the residue discarded. Ammonium sulfate (32 g) was slowly added to the supernatant until the mixture became turbid. After 1 h at 48 C a white precipitate formed which was removed by centrifugation at 13,000 g for 10 min. Ammonium sulfate (18 g) was added to the resulting clear blue supernatant solution followed by centrifugation at 13,000 g for 15 min. The blue precipitate was dissolved in 35 ml of Tris buffer (50 mM Tris-HCl buffer, pH 7.0). Ammonium sulfate was removed by ultrafiltration. The concentrated solution (168 mg protein) was applied to a Q-Sepharose column (2.6×40 cm2) that had previously been equilibrated with Tris buffer. The column was washed with 200 ml of the same buffer at a flow rate of 1.0 ml per min. Bound protein was eluted with a 600 ml linear gradient (0.0-0.5 M) of KCl in Tris buffer. Blue-colored fractions, eluting at ~0.3 M KCl, were pooled and concentrated to 4.8 ml (10.1 mg of protein) by ultrafiltration.

Ammonium sulfate (4.0 M) was added to the concentrated solution to give a final concentration of 1.0 M. The solution was clarified by centrifugation at 13,000 g for 10 min and applied to the top of a Phenyl Sepharose High-Performance Column (5.0×1.0 ml$^2$) that had previously been equilibrated with Tris buffer containing 1.0 M (NH4)2SO4. The column was washed with the same buffer at a flow rate of 1.0 ml per min until protein was no longer detected in the eluate. Bound protein was eluted with a linear gradient of (NH4)2SO4 (1.0-0.0 M) in the same buffer.

Blue-colored fractions were pooled and concentrated by ultrafiltration. Ammonium sulfate was removed by buffer exchange with 5.0 mM KH2PO4, pH 7.0. This preparation (5.0 mg of protein) was applied to a ceramic hydroxyapatite XK16/70 column (80×1.0 ml2) that had been equilibrated with 5.0 mM KH2PO4 buffer, pH 7.0. Unbound protein was eluted with 100 ml of the same buffer at a flow rate of 1.0 ml per min before initiating a linear gradient (5-200 mM) of KH2PO4 buffer, pH 7.0. Dark blue fractions (1.0 ml) eluting from the column were pooled, concentrated by ultrafiltration and exchanged into 10 mM KH2PO4 buffer, pH 7.0, before adding in 30 ml aliquots to liquid nitrogen. The resulting pellets were stored at −70° C.

Protein Determination. Protein concentrations were determined by the method of Bradford (Bradford 1976) using bovine serum albumin as the standard.

Electrophoresis. Protein purity and subunit molecular weights were determined by sodium dodecyl sulfate polyacrylamide gel electrophoresis (SDS-PAGE) on 12.5% gels (Laemmli 1970). Samples were boiled for 6 min prior to loading onto the gels. Protein standards used for the estimation of subunit molecular masses were Low-Range Molecular Weight SDS-PAGE Standards (Bio-Rad Laboratories). Protein bands were stained with Coomassie Brilliant Blue R250.

Molecular Mass. The molecular mass and subunit molecular mass of the blue protein was determined by matrix-assisted laser desorption ionization-time of flight/mass spectrometry (MALDI-TOF/MS) at The University of Iowa Molecular Analysis Facility, using a-cyano-4-hydroxycinnamic acid (CHCA) in 50% acetonitrile: 50% 0.1% trifluoroacetic acid as matrix.

Cyanogen Bromide Cleavage. A small crystal of cyanogen bromide was added to 50 ml of formic acid (70%) containing purified blue protein (15 mg). The reaction mixture was incubated in the dark at 258 C for 24 h and then taken to dryness.

Proteolytic Digestion. In separate experiments, purified blue protein was digested with endoproteinases Glu-C, Arg-C, Lys-C, and Asp-C, at ratios of endoproteinase to blue protein recommended by the supplier (Sigma Chemical Co., St. Louis, Mo.). Reaction mixtures were incubated at 378 C for 2-18 h and then taken to dryness.

Amino Acid Sequence Determination. Peptides produced by cyanogen bromide cleavage and proteolytic digestion were separated by SDSPAGE, electroblotted onto polyvinylidene membranes and their respective amino acid sequences determined by Edman degradation on an automated amino acid sequencer (Applied Biosystems, Foster City, Calif.) at The University of Iowa Molecular Analysis Facility.

Transition Metals. Transition metals were investigated by inductively coupled plasma mass spectrometry (ICP-MS) on a VG PlasmaQuad II ICP-MS machine at the University of Iowa Hygienic Laboratory, Des Moines, Iowa.

Example 3

Preparation and Isolation of Recombinant Sandercyanin Protein

In this example, the inventors describe how to isolate and purify the recombinant Sandercyanin protein according to SEQ ID NO: 2 of the present invention.

SEQ ID NO: 2. Sequence of recombinant Sandercyanin protein.

```
                                              (SEQ ID NO: 2)
MFIKPGRCPKPAVQEDFDAARYLGVWYDIQRLPNKFQKGECATATYSLSP

GVGFSVFNRERLANGTIKSVIGSAIAEDPCEPAKLQFFHENAAPVPYWVL

STDYDNYALVYSCINLGASHAAYASIVSRQPTLPEETIKKLQGTMSSFGV

GVDTLLTTNQDAAYCSAMNQ.
```

In one embodiment, the recombinant Sandercyanin protein of SEQ ID NO: 2 can be prepared using the *E. coli* expression system (known to the art). For instance, by expressing the recombinant Sandercyanin protein of SEQ ID NO: 2 in M9 minimal media, followed by Ni-NTA affinity purification and size-exclusion chromatography, the recombinant Sandercyanin protein of SEQ ID NO: 2 is prepared. This method yields smaller amounts of protein, as limited amounts of nutrients in media are used. However, the isolated protein is soluble.

In other embodiments, by refolding the protein from inclusion bodies (IBs) in presence of 5 mM/1 mM of L-cysteine/L-cystine redox system, the recombinant Sandercyanin protein of SEQ ID NO: 2 can also be prepared. IBs are solubilized using 5M guanidine, HCl followed by rapid dilution in 1M guanidine, HCl and successive two-step dialysis in 0.375M and O M guanidine, and HCl buffers. Using this method, large quantities of soluble and functional recombinant Sandercyanin protein of SEQ ID NO: 2 are recovered from the IBs.

The inventors also describe various expression vectors the Sandercyanin protein can be expressed in. For instance, in one embodiment, the gene for Sandercyanin protein (SEQ ID NO: 2) was cloned into bacterial expression vector pET21a with C-terminal 6×His-tag. The protein was isolated from inclusion bodies, refolded and purified by dialysis.

Inclusion bodies (IBs) were isolated from the bacterial pellet (2 L) after sonication for 5 minutes with 10 s on and off cycles and centrifuged at 16,000 RPM. IBs were re-suspended in 5M guanidine. HCl and refolded by rapid dilution and two step dialysis process. Spectroscopic studies of the refolded protein show that the protein had refolded to its active form with the fluorescence similar to the native protein from the fish.

Other common bacterial expression vectors for the suitable expression of fluorescent proteins are readily known to one of skill in the art.

Example 4

Descriptions of Transgene Incorporation into Biomolecules

In this example, the inventors describe how one of skill would incorporate the recombinant Sandercyanin gene (as set forth in SEQ ID NO: 2) in different mammalian cells-lines. One of skill in the art will be familiar with these techniques.

In one embodiment, the Sandercyanin gene can be incorporated as a fusion tag with a protein of interest for intracellular localization in cell-culture.

In one embodiment, the Sandercyanin gene can be incorporated as a fusion partner to generate transgenic animals.

In one embodiment, the Sandercyanin gene can be incorporated as cell surface marker (as the Sandercyanin protein is a secreted protein).

In one embodiment, the Sandercyanin gene can be used as a mitochondrial marker (as biliverdin production occurs in mitochondria).

Example 5

Applications of Isolated Sandercyanin Protein

In this example, the inventors describe how one of skill would incorporate the Sandercyanin protein into various biomolecules as a fluorescence marker. One of skill in the art will be familiar with these techniques.

For instance, in one embodiment, when Sandercyanin protein (as set forth in SEQ ID NO: 1 and SEQ ID NO: 2) is injected into hydra (a model system to study regeneration), showed fluorescence on the surface of tentacles. We are currently imploring the localization of Sandercyanin in model organisms.

Commercial Embodiments of the Invention.

Sandercyanin's unique ability to be excited at a relatively low and distant wavelength with respect to its emission wavelength lends itself to many commercial applications. Specifically, Sandercyanin can be used for imaging proteins, studying protein dynamics and other molecular complexes inside cells, which allows it to be used in a variety of areas of modern bioscience and biomedical research. It can also be used for tracking macromolecule movement in living cells due to near infra-red emission, as well as work as a reporter for stable cell lines, therapeutic viral incorporation and replication experiments.

In addition, a researcher could potentially use this technology for replacing quantum dots (Q-dots) for monitoring vasculature during in vivo imaging studies. Quantum dots are nanocrystals with unique chemical properties that provide tight control over the spectral characteristics of the fluorophore. They are nanoscale-sized (2-50 nm) semiconductors that, when excited, emit fluorescence at a wavelength based on the size of the particle; smaller quantum dots emit higher energy than large quantum dots, and therefore the emitted light shifts from blue to red as the size of the nanocrystal increases. Because quantum dot size can be tightly controlled, there is greater specificity for distinct excitation and emission wavelengths than other fluorophores. While the use of quantum dots in biological applications is increasing, there are reports of cell toxicity in response to the breakdown of the particles and their use can be cost-prohibitive.

Besides being able to use the Sandercyanin in many of the applications where Green Fluorescent Proteins are currently used, one can also use it for detection of proteins (protein interaction in Fluorescence Resonance Energy Transfer—FRET). Specifically, the large energy difference in excitation may allow for a clearer signal if the Sandercyanin protein is used in combination with a Cy5 based dye.

For instance, the Sandercyanin protein may be used in near infrared optical imaging. The Sandercyanin protein provides superior advantages over existing fluorescent proteins and features, which provide benefits missing in existing technologies. For instance, the Sandercyanin protein has a large Stokes shift (~300 nm) with absorption and emission at 375 nm and 675 nm, respectively, which stands out when compared to existing proteins. Stokes shift is the difference in wavelength between positions of the band maxima of the absorption and emission spectra and is an important factor when fluorescence is considered. The longer the Stokes shift, the better for the researcher because associated absorption and emission light wavelength separation is key for effective imaging.

The Sandercyanin protein also has improved quenching time, which will provide fluorescence with extra-long quenching time when compared to existing technologies.

Half-life is another important factor that influences the quality of the protein being used as well as brightness, in which Sandercyanin also stands out for being a stable protein with high brightness as compared to other fluorescent proteins.

Finally, the Sandercyanin protein does not require cofactors to exhibit intrinsic fluorescence whereas other fluorescent proteins do require them.

Further, fluorophores in the far red and near infrared region (~650-850 nm) are useful for in vivo optical imaging, where the expression of Sandercyanin, either alone or tagged to another target protein, could be monitored in a live animal model (mouse, rat, zebrafish, etc.). An advantage to in vivo imaging is that complex tumor and/or normal tissue models can be developed and tested. For example, murine tumor models may behave very differently than cells cultured in vitro, as the animal model allows for the complex mix of normal tissue cells, tumor vascular supply and endothelial cells, supporting cells, along with the tumor cell being tested, to grow and behave much more like a "real" tumor would behave.

Spectral properties of Sandercyanin would allow for excitation of the agent in the short wavelength near UV/UV spectrum and emission in the NIR (FIGS. 1-11). Currently, there are no commercially available imaging agents, with the exception of toxic (cadmium containing) quantum dots. The current invention would allow for the spectral red shift only available with quantum dots to be used in vivo.

One example for the use of in vivo optical imaging using Sandercyanin is in expression of Sandercyanin in cancer cell lines for grafting into mice. Sandercyanin could be used as an alternative to GFP and Luciferase as a reporter to follow tumor size and/or response to treatment via in vivo optical imaging. This would be done through incorporation of the Sandercyanin gene into desired cell lines via standard lentiviral methods to develop a stable transgenic line. Sandercyanin would then act as the in vivo reporter gene. This would be less costly, as there would be no need for injections of a substrate (luciferin) and imaging would take less time as the NIR reporter could be directly imaged without additional substrates.

Further uses of the claimed inventions include using the protein for reporter stable cell lines or using it as a reporter for monitoring tumor growth. In some embodiments, Sandercyanin could take the place of GFP and/or luciferase as a reporter for therapeutic viral incorporation and replication experiments. The use of therapeutic viruses, such as conditionally replicative adenoviruses, has become a more desirable method for treating various cancers. Currently, these are studied in the laboratory in vitro and in vivo. To determine viral infectivity, GFP is often used as the reporter gene product. However, when translated in vivo this becomes difficult as GFP is not able to penetrate through tissue. Similar to the above, luciferase can be used, however, you are limited in the number of time points data can be collected by the requirement of the substrate luciferin to be injected into the animals. Sandercyanin could be used as a reporter both in vitro and in vivo, limiting the number of "unnatural" gene products produced by therapeutic viral constructs (i.e., both GFP and luciferase) and would offer the ability for nearly continuous monitoring of viral infection via NIR imaging in host animals.

Additionally, Sandercyanin could be used as a direct replacement for GFP or similar molecules in confocal microscopy, flow cytometry, fluorescence microscopy, and other optical based spectroscopy methods. Again, the unique spectral properties would allow for Sandercyanin to be incorporated with other fluorophores without overlap of excitation/emission spectra, allowing for Sandercyanin to be visualized without interference by other fluorescent proteins. Sandercyanin would allow for a greater spectral range in confocal microscopy studies. For the above reason it could be used with other far-red dyes yet theoretically have little signal overlap as the excitation would be significantly far apart in the spectrum. Being monomeric, Sandercyanin could be used in fusion gene products, such as GFP, to monitor the subcellular localization of proteins.

Sandercyanin could replace Q-dots on nanoparticles that monitor vasculature during in vivo imaging studies. Similarly, it offers a unique ability to be incorporated as a fusion to single chain variable fragments or in the construct of engineered antibodies. Currently, in vivo imaging of antibodies requires the chemical conjugation of dyes or Q-dots to antibodies to do this. Conjugation of these dyes can significantly decrease affinity to antigen as the reporter molecules may cross link in the space.

Additionally, Sandercyanin may be used in fluorescence resonance transfer experiments. The large energy difference in excitation may allow for a clearer signal if this was used in pair with a Cy5 based dye.

Expression in cancer cell lines for grafting into mice. Sandercyanin could be used as an alternative to GFP and Luciferase as a reporter to follow tumor size and/or response to treatment via in vivo optical imaging. This would be done through incorporation of the Sandercyanin gene into desired cell lines via standard lentiviral methods to develop a stable transgenic line. This line can be sorted in vitro using flow cytometry directly using Sandercyanin as the reporter if needed prior to tumor initiation. Sandercyanin could take the place of luciferase as the in vivo reporter gene. This would be less costly, as there would be no need for injections of a substrate (luciferin) and imaging would take less time as the NIR reporter could be directly imaged without additional substrates.

In other embodiments, the Sandercyanin protein of the present invention could take the place of GFP and or luciferase as a reporter for therapeutic viral incorporation and replication experiments. The use of therapeutic viruses, such as conditionally replicative adenoviruses, has become a more desirable method for treating various cancers. Currently, these are studied in the laboratory in vitro and in vivo. To determine viral infectivity, GFP is often used as the reporter gene product. However, when translated in vivo this becomes difficult as GFP is not able to penetrate through tissue. Similar to the above, luciferase can be used, however, you are limited in the number of time points data can be collected by the requirement of the substrate luciferin to be injected into the animals. Sandercyanin could be used as a reporter both in vitro and in vivo, limiting the number of "unnatural" gene products produced by therapeutic viral constructs (i.e., both GFP and luciferase) and would offer the ability for nearly continuous monitoring of viral infection via NIR imaging in host animals.

Sandercyanin would allow for a greater spectral range in confocal microscopy studies. For the above reason it could be used with other far-red dyes yet theoretically have little signal overlap as the excitation would be significantly far apart in the spectrum. Being monomeric, Sandercyanin could be used in fusion gene products, such as GFP, to monitor the subcellular localization of proteins.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Abraham et al. 2008. Pharmacological Reviews 60:79-127.
Allanson et al. 2005. Journal of Investigative Dermatology 124:644-650.
Arkin et al. 1990. Bio-Technology 8: 746-749.
Bada J. L. 1970. Experientia 26:251-259.
Bellner et al. 2011. Investigative Ophthalmology & Visual Science 52:3246-3253.
Blazer et al. 1997. Journal of Aquatic Animal Health 9:132-143.
Campbell, R. R. 1987. Canadian Field-Naturalist 101:245-252.
Chiesa et al. 2001. Biochemical J., 355(Part 1): 1-12.
Chivers et al. Proceedings of the Royal Society B-Biological Sciences 274:2611-2619.
Cubitt et al. 1995. Trends In Biochemical Sciences, 20(11): 448-455.
Deheyn et al. 2009. Invertebrate Biology 128:31-45.
Dunlap et al. 1998. Journal of Phycology 34:418-430.
Elassiuty et al. 2011. Experimental Dermatology 20:496-501.
Fabacher et al. 1995. Environmental Science and Pollution Research 2:30-32.
Fang, L. S. 1985. Bulletin of the Institute of Zoology Academia Sinica (Taipei) 24:155-164.
Fang et al. 1983. Marine Biology Letters 4:341-348.
Flower, D. R. 1996. Biochemical Journal 318:1-14.
Frankenberg et al. 2003. Pp. 211-235 In: The Porphyrin Handbook. Chlorophylls and Bilins: Biosynthesis Structure and Degradation., K. M. Kadish, K. M. Smith, and R. Guilard, Editors. Academic Press: New York.
Gagnon, M. M. 2006. Journal of Fish Biology 68:1879-1882.
Hansson, L. A. 2004. Ecology 85:1005-1016.
Hansson et al. 2009. Photochemical & Photobiological Sciences 8:1266-1275.
Inoue et al. 2009. Journal of Biochemistry 145:169-175.
Jonsson et al. 2011. Journal of Fish Biology 79:290-297.
Kerr et al. 1993. Science 262:1032-1034.
Kollias et al. 1991. Journal of Photochemistry and Photobiology B-Biology 9:135-160.
Lagarias et al. 1989. Proc. Natl. Acad. Sci. USA, 86(15): 5778-5780.
Lamparter et al. 2002. Proc. Natl. Acad. Sci. USA, 99(18): 11628-11633.
Leclercq et al. 2010. Fish and Fisheries 11:159-193.
Manney et al. 2011. Nature 478:469-U465.
Marrot et al. 2005. Photochemistry and Photobiology 81:367-375.
Murphy et al. 1997. Current Biology, 7: 870-876.
Paradis et al. 2005. Environmental Biology of Fishes 73:357-366.
Pickering et al. 1987. Cell and Tissue Research 247:259-265.
Rastogi et al. 2010. Journal of Industrial Microbiology & Biotechnology 37:537-558.
Reeve et al. 2006. Photochemistry and Photobiology 82:406-411.
Reeve et al. 1999. Proceedings of the National Academy of Sciences of the United States of America 96:9317-9321.
Scott et al. 1973. Freshwater fishes of Canada.
Schmitz, M. H. 2011. Ph.D. Dissertation, University of Wisconsin—Milwaukee. 110 p.
Whitaker et al. 1980. Analytical Biochemistry 109:156-159.
Whitear, M. 1986. The skin of fishes including cyclostomes. Pages 8-64 in J. Bereiter-Hahn, A. G. Matoltsy, and K. S. Richards, editors. Biology of the Integument. Springer, Berlin Heidelberg, New York.
Yamaguchi et al. 1976. Comparative Biochemistry and Physiology B-Biochemistry & Molecular Biology 55:85-87.
Yannarelli et al. 2006. Planta 224:1154-1162.
Yu et al. 2007. Environmental Biology of Fishes 82:51-58.
Zagarese et al. 2001. Fish and Fisheries 2:250-260.

We claim:

1. A method of preparing a fluorescent probe, the method comprising attaching a Sandercyanin fluorescent protein moiety to a probe for detecting a specific target wherein the Sandercyanin fluorescent protein moiety is selected from the group consisting of SEQ ID NO:1 and SEQ ID NO:2.

2. A fluorescent probe, comprising a Sandercyanin fluorescent protein moiety and a probe for detecting a specific target wherein the Sandercyanin fluorescent protein moiety is selected from the group consisting of SEQ ID NO:1 and SEQ ID NO:2.

3. The fluorescent probe of claim 1, wherein the probe is selected from the group consisting of antibodies, proteins and enzymes.

4. The fluorescent probe of claim 1, wherein the probe emits a fluorescent signal.

5. The fluorescent probe of claim 1, wherein the target is a biomolecule.

6. A method of using a fluorescent probe, comprising the steps of
   a. obtaining the fluorescent probe of claim 2,
   b. exposing the fluorescent probe to a desired target, and
   c. exposing the probe and target to light having a wavelength ranging from about 350-690 nm,
   wherein the fluorescent probe fluoresces.

7. The method of claim 6, wherein the target is a biomolecule.

8. A labeled marker for detection of a target, the marker comprising a ligand configured to bind to the target and a Sandercyanin protein moiety wherein the Sandercyanin protein moiety is selected from the group consisting of SEQ ID NO:1 and SEQ ID NO:2.

9. The marker of claim 8 wherein the ligand is selected from the group consisting of a nucleic acid probe, an antibody, biotin, avidin and streptavidin.

10. A method for detecting a target comprising:
    a. providing a labeled ligand which comprises a ligand for binding the target and a Sandercyanin fluorescent protein label, wherein the Sandercyanin protein moiety is selected from the group consisting of SEQ ID NO:1 and SEQ ID NO:2, and a ligand for binding the target;
    b. contacting the target with the labeled ligand;
    c. allowing the labeled ligand to bind to the target;
    d. subjecting the labeled ligand and target to light having a wavelength which excites the label; and
    e. observing the locus of fluorescence.

\* \* \* \* \*

SEQUENCE LISTING

<160> NUMBER OF SEQ ID NOS: 2

<210> SEQ ID NO 1
<211> LENGTH: 170
<212> TYPE: PRT
<213> ORGANISM: Sandercyanin

<400> SEQUENCE: 1

```
Gln Phe Ile Lys Pro Gly Arg Cys Pro Lys Pro Ala Val Gln Glu Asp
1               5                   10                  15

Phe Asp Ala Ala Arg Tyr Leu Gly Val Trp Tyr Asp Ile Gln Arg Leu
            20                  25                  30
```

```
Pro Asn Lys Phe Gln Lys Gly Glu Cys Ala Thr Ala Thr Tyr Ser Leu
        35                  40                  45

Ser Pro Gly Val Gly Phe Ser Val Phe Asn Arg Glu Arg Leu Ala Asn
    50                  55                  60

Gly Thr Ile Lys Ser Val Ile Gly Ser Ala Ile Ala Glu Asp Pro Cys
 65              70                  75                      80

Glu Pro Ala Lys Leu Gln Phe Phe His Glu Asn Ala Ala Pro Val Pro
                85                  90                      95

Tyr Trp Val Leu Ser Thr Asp Tyr Asp Asn Tyr Ala Leu Val Tyr Ser
                100                 105                 110

Cys Ile Asn Leu Gly Ala Ser His Ala Ala Tyr Ala Ser Ile Val Ser
            115                 120                 125

Arg Gln Pro Thr Leu Pro Glu Glu Thr Ile Lys Lys Leu Gln Gly Thr
            130                 135                 140

Met Ser Ser Phe Gly Val Gly Val Asp Thr Leu Leu Thr Thr Asn Gln
145                 150                 155                 160

Asp Ala Ala Tyr Cys Ser Ala Met Asn Gln
                165                 170

<210> SEQ ID NO 2
<211> LENGTH: 170
<212> TYPE: PRT
<213> ORGANISM: Sandercyanin

<400> SEQUENCE: 2

Met Phe Ile Lys Pro Gly Arg Cys Pro Lys Pro Ala Val Gln Glu Asp
 1               5                  10                  15

Phe Asp Ala Ala Arg Tyr Leu Gly Val Trp Tyr Asp Ile Gln Arg Leu
                20                  25                  30

Pro Asn Lys Phe Gln Lys Gly Glu Cys Ala Thr Ala Thr Tyr Ser Leu
            35                  40                  45

Ser Pro Gly Val Gly Phe Ser Val Phe Asn Arg Glu Arg Leu Ala Asn
    50                  55                  60

Gly Thr Ile Lys Ser Val Ile Gly Ser Ala Ile Ala Glu Asp Pro Cys
 65              70                  75                      80

Glu Pro Ala Lys Leu Gln Phe Phe His Glu Asn Ala Ala Pro Val Pro
                85                  90                      95

Tyr Trp Val Leu Ser Thr Asp Tyr Asp Asn Tyr Ala Leu Val Tyr Ser
                100                 105                 110

Cys Ile Asn Leu Gly Ala Ser His Ala Ala Tyr Ala Ser Ile Val Ser
            115                 120                 125

Arg Gln Pro Thr Leu Pro Glu Glu Thr Ile Lys Lys Leu Gln Gly Thr
            130                 135                 140

Met Ser Ser Phe Gly Val Gly Val Asp Thr Leu Leu Thr Thr Asn Gln
145                 150                 155                 160

Asp Ala Ala Tyr Cys Ser Ala Met Asn Gln
                165                 170
```